(12) United States Patent
Mather

(10) Patent No.: US 7,744,878 B2
(45) Date of Patent: Jun. 29, 2010

(54) ANTIBODIES THAT BIND TO CANCER-ASSOCIATED ANTIGEN CD46 AND METHODS OF USE THEREOF

(75) Inventor: Jennie P. Mather, Millbrae, CA (US)

(73) Assignee: Raven biotechnologies, inc., South San Francisco, CA (US)

( * ) Notice: Subject to any disclaimer, the term of this patent is extended or adjusted under 35 U.S.C. 154(b) by 225 days.

(21) Appl. No.: 11/524,344

(22) Filed: Sep. 19, 2006

(65) Prior Publication Data

US 2007/0128202 A1 Jun. 7, 2007

Related U.S. Application Data

(63) Continuation of application No. 10/272,835, filed on Oct. 16, 2002, now Pat. No. 7,148,038.

(60) Provisional application No. 60/329,644, filed on Oct. 16, 2001.

(51) Int. Cl.
*A61K 39/00* (2006.01)

(52) U.S. Cl. ............... 424/133.1; 424/138.1; 424/155.1; 424/174.1; 424/181.1; 424/183.1; 530/350; 530/387.3; 530/387.7; 530/388.8; 530/389.7; 530/391.3; 530/391.7

(58) Field of Classification Search ............... 424/138.1, 424/155.1, 174.1, 181.1, 183.1, 133.1; 530/350, 530/387.7, 388.8, 389.7, 391.3, 391.7, 387.3
See application file for complete search history.

(56) References Cited

U.S. PATENT DOCUMENTS

| | | | |
|---|---|---|---|
| 4,816,567 | A | 3/1989 | Cabilly et al. |
| 5,514,787 | A | 5/1996 | Atkinson |
| 5,552,381 | A | 9/1996 | Atkinson |
| 5,665,570 | A | 9/1997 | Yamagata et al. |
| 5,677,425 | A | 10/1997 | Bodmer et al. |
| 5,703,046 | A | 12/1997 | Atkinson |
| 5,760,185 | A | 6/1998 | Kimachi et al. |
| 5,773,247 | A | 6/1998 | Maeda et al. |
| 5,807,715 | A | 9/1998 | Morrison et al. |
| 5,846,715 | A | 12/1998 | Purcell et al. |
| 5,866,692 | A | 2/1999 | Shitara et al. |
| 5,929,212 | A | 7/1999 | Jolliffe et al. |
| 5,932,225 | A | 8/1999 | Wallach et al. |
| 5,997,867 | A | 12/1999 | Waldmann et al. |
| 6,054,297 | A | 4/2000 | Carter et al. |
| 6,086,876 | A | 7/2000 | Karp et al. |
| 6,110,724 | A | 8/2000 | Nakagomi et al. |
| 6,117,653 | A | 9/2000 | Thoma |
| 6,180,377 | B1 | 1/2001 | Morgan et al. |
| 6,210,671 | B1 | 4/2001 | Co |
| 6,218,520 | B1 * | 4/2001 | Atkinson .................. 536/23.1 |
| 6,221,644 | B1 | 4/2001 | Berka et al. |
| 6,331,415 | B1 | 12/2001 | Cabilly et al. |
| 6,350,861 | B1 | 2/2002 | Co et al. |
| 6,441,163 | B1 | 8/2002 | Chari et al. |
| 7,148,038 | B2 | 12/2006 | Mather |
| 2002/0115065 | A1 | 8/2002 | Logtenberg et al. |
| 2003/0108966 | A1 * | 6/2003 | Mather ....................... 435/7.23 |
| 2003/0129677 | A1 * | 7/2003 | Martens et al. ............. 435/7.23 |
| 2004/0045045 | A1 * | 3/2004 | Mather et al. .................. 800/14 |
| 2005/0037439 | A1 * | 2/2005 | Bourner et al. .............. 435/7.2 |
| 2008/0108794 | A1 * | 5/2008 | Goldenberg et al. ..... 530/387.3 |

FOREIGN PATENT DOCUMENTS

| | | |
|---|---|---|
| EP | 0 519 596 A1 | 12/1992 |
| WO | WO-01/27160 A1 | 4/2001 |
| WO | WO-01/88537 A1 | 11/2001 |
| WO | WO-02/18948 A2 | 3/2002 |
| WO | WO-02/18948 A3 | 3/2002 |
| WO | WO-03/032814 A2 | 4/2003 |
| WO | WO-03/032814 A3 | 4/2003 |

OTHER PUBLICATIONS

Reimer et al. (J. Immunol. 2004; 174: 394-401).*
Jurianz et al. (Immunopharmacol. 1999; 42: 209-218).*
Fishelson et al. (Mol. Immunol. 2003; 40: 109-123).*
Wojnicz et al. (Postepy. Hig. Med. Dosw. 2002; 56 (5): 603-616).*
Pollard et al. (Gene. 1998; 212: 39-47).*
Nomura et al. (Immunogenetics. 1999 50: 245-254).*
Hara et al. (Scand. J. Immunol. 1995; 42: 581-590).*
Purcell et al. (Immunogenetics. 1991; 33: 335-344).*
Seya et al. (Int. J. Biochem. Cell Biol. 1999; 31: 1255-1260).*
Caldas et al. (Mol. Immunol. May 2003; 39 (15): 941-952).*
Stancoviski et al. (Proceedings of the National Academy of Science USA. 1991; 88: 8691-8695).*
Jiang et al. (J. Biol. Chem. Feb. 11, 2005; 280 (6): 4656-4662).*
Riemer et al. (Mol. Immunol. 2005; 42: 1121-1124).*
Henry et al. (Cancer Res. Nov. 1, 2004; 64: 7995-8001).*
McDevitt et al. (Cancer Res. Nov. 1, 2000; 60: 6095-6100).*
Ollert et al. (J. Immunol. 1995; 155: 4955-4962).*
Gorter et al. (Lab. Investig. 1996; 74: 1039-1049).*
Maenpaa et al. (Am. J. Pathol. 1996; 148: 1139-1152).*
Dillman (Curr. Pharmaceut. Biotechnol. 2001; 2: 293-300).*
Weiner et al. (Semin. Oncol. 1999; 26: 43-51).*
Loberg et al. (Urology. Dec. 2005; 66 (6): 1321-1326).*
Goslings et al. (Investig. Ophthalmol. Vis. Sci. 1996; 37: 1884-1891).*
Gelderman et al. (Mol. Immunol. 2003; 40: 13-23).*
Niehans et al. (Am. J. Pathol. 1996; 149: 129-142).*
Bodey et al. (Anticancer Res. 2000; 20: 2665-2676).*
Lollini et al. (Curr. Cancer Drug Targets. May 2005; 5 (3): 221-228).*
Lollini et al. (Trends Immunol. Feb. 2003; 24 (2): 62-66).*
Slinghuff et al. (Cancer Immunol. Immunother. Mar. 2000; 48 (12): 661-672).*

(Continued)

*Primary Examiner*—Stephen L Rawlings
(74) *Attorney, Agent, or Firm*—Jeffrey I. Auerbach; Edell, Shapiro & Finnan, LLC

(57) ABSTRACT

Provided herein is disclosure about the development and characterization of an antibody (mPA7) which binds to antigen CD46 which is present on a variety of human cancers from ovary, breast, lung, prostate, colon, kidney, and pancreas. Methods of diagnosing and treating various cancers by using antibodies such as mPA7 directed against this antigen are also disclosed.

6 Claims, 5 Drawing Sheets

OTHER PUBLICATIONS

Madjd et al. (Cancer Immunol. Immunother. 2005; 54: 149-156).*
Rushmere et al. (Int. J. Cancer. Mar. 1, 2004; 108 (6): 930-936).*
Blok et al. (Lab. Invest. Mar. 2000; 80 (3): 335-344).*
Gura (Science. 1997; 278: 1041-1042).*
Dennis (Nature. Aug.7, 2006; 442: 739-741).*
Kelland (Eur. J. Cancer. Apr. 2004; 40 (6): 827-836).*
Schuh (Toxicologic Pathology. 2004; 32 (Suppl. 1): 53-66).*
Suggitt et al. (Clin. Cancer Res. Feb. 1, 2005; 11: 971-981).*
Greenspan et al. (Nature Biotechnology. 1999; 7: 936-937).*
Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Weng et al. (Blood. Sep. 1, 2001; 98 (5): 1352-1357).*
Zell et al. (Clin. Exp. Immunol. Dec. 2007; 150 (3): 576-584).*
Liszewski et al. (Curr. Top. Microbiol. Immunol. 1992; 178: 45-60).*
Adams, E.M. et al. (Nov. 1, 1991). "Contribution of the Repeating Domains of Membrane Cofactor Protein (CD46) of the Complement System to Ligand Binding and Cofactor Activity," *The Journal of Immunology* 147(9):3005-3011.
Allen, B.J. et al. (2001). "In Vitro and Preclinical Targeted Alpha Therapy for Melanoma, Breast, Prostate and Colorectal Cancers," *Crit. Rev. Oncol. Hmatol.* 39:139-146.
Andrew, S.M. et al. (1990). "Tumor Localizations by Combinations of Monoclonal Antibodies in a New Human Colon Carcinoma Cell Line (LIM1899)," *Cancer Res.* 50: 5225-30.
Aruffo, A. et al. (1987). "Molecular Cloning of a CD28 cDNA by High-Efficiency COS Cell Expression System," *Proc. Natl. Acad. Sci. USA* 84:8573-8577.
Azuma, A. et al. (1995). "Augmented Lung Adenocarcinoma Cytotoxicity by the Combination of a Genetically Modified Anti-Lewis Y Antibody and Antibodies to Complement Regulatory Proteins," *Scand. J. Immunol.* 42: 202-208.
Ballard, L. et al. (1987). "A Polymorphism of the Complement Regulatory Protein MCP (Membrane Cofactor Protein or gp45-70)," *J. Immunol.* 138(11):3850-3855.
Bjorge, L. et al. (1996). "Characterisation of the Complement-Regulatory Proteins Decay-Accelerating Factor (DAF, CD55) and Membrane Cofactor Protein (MCP, CD46) on a Human Colonic Adenocarcinomic Cell Line," *Cancer Immunol. Immunother.* 42:185-192.
Bjorge, L. et al. (1997). "Complement-Regulatory Proteins in Ovarian Malignancies," *Int. J. Cancer* 70:14-25.
Blok, V.T. et al. (2000). "A Possible Role of CD46 for the Protection In Vivo of Human Renal Tumor Cells from Complement-Mediated Damage," *Lab. Invest.* 80(3):335-44.
Blom, D-J. et al. (1997). "Lack of Effect of Different Cytokines on Expression of Membrane-Bound Regulators of Complement Activity on Human Uveal Melanoma Cells," *J Interferon Cytokine Res.* 17(11):695-700.
Brown, B.A. et al. (1987). "Tumor-Specific Genetically Engineered Murine/Human Chimeric Monoclonal Antibody," *Cancer Research* 47:3577-3583.
Buchholz, C.J. et al. (Aug. 29, 1997). "Mapping of the Primary Binding Site of Measles Virus to its Receptor CD46," *Journal of Biological Chemistry* 272(35):22072-22079.
Cho, S-W. et al. (1991). "Characterization of Three Monoclonal Antibodies to Membrane Co-Factor Protein (MCP) of the Complement System and Quantification of MCP by Radioassay," *Clin. Exp. Immunol.* 83:257-261.
Cole, J.L. et al. (1985). "Identification of an Additional Class of C3-Binding Membrane Proteins of Human Peripheral Blood Leukocytes and Cell Lines," *Proc. Natl. Acad. Sci.* USA 82:859-869.
Daugherty, B.L. et al. (1991). "Polymerase Chain Reaction Facilitates the Cloning, CDR-Grafting, and Rapid Expression of a Munine Monoclonal Antibody Directed Against the CD 18 Component of Leukocyte Integrins," *Nucleic Acids Research* 19(9):2471-2476.

Dillman, R.O. et al. (1988). "Superiority of an Acid-Labile Daunorubicin_Monoclonal Antibody Immonoconjugate Compared to Free Drug," *Cancer Research* 48:6097-6102.
Donin, N. et al. (2003). "Complement Resistance of Human Carcinoma Cells Depends on Membrane Regulatory Proteins, Protein Kinases and Sialic Acid," *Clin. Exp. Immunol.* 131:254-263.
Durrant, L.G. et al. (Jul. 2001). "Immunization Against Tumor Cell Surface Complement-Regulatory Proteins," *Current Opinion in Investigational Drugs* 2(7):959-966.
Fénichel, P. et al. (1990). "Localization and Characterization of the Acrosomal Antigen Recognized by GB24 on Human Spermatozoa," *Molecular Reproduction and Development* 27:173-178.
Flieger, D. et al. (2001). "Influence of Cytokines, Monoclonal Antibodies and Chemotherapeutic Drugs on Epithelial Cell Adhesion Molecule (EpCAM) and Lewis$^Y$ Antigen Expression," *Clin. Exp. Immunol.* 123:9-14.
Fracasso, G. et al. (2002). "Anti-Tumor Effects of Toxins Targeted to the Prostate Specific Membrane Antigen," *Prostate* 53:9-23.
Gennaro, A.R. ed. (2000). *Remington: The Science and Practice of Pharmacy.* 20$^{th}$ edition, Mack Publishing, (Table of Contents Only.).
Goldenberg, D.M. ed. (1995). *Cancer Therapy with Radiolabeled Antibodies.* CRC Press, Inc: Boca Raton, FL, four pages, (Table of Contents Only.).
Gorter, A. et al. (1996). "Expression of CD46, CD55, and CD 59 on Renal Tumor Cell Lines and Their Role in Preventing Complement-Mediated Tumor Cell Lysis," *Lab. Invest.* 74(6):1039-1049.
Hofman, P. et al. (1994). "High Expression of the Antigen Recognized by the Monoclonal Antibody GB24 on Human Breast Carcinomas: A Preventive Mechanism of Malignant Tumor Cells Against Complement Attack?" *Breast Cancer Res. Treat.* 32:213-219.
Hsi, B.L. (1988). "Monoclonal antibody GB24 Recognizes a Trophoblast-Lymphocyte Cross-Reactive Antigen," *Am. J. Reprod. Immunol. Microbiol.* 18(1):21-27.
Hsu, E.C. et al. (Jun. 5, 1999). "Use of Site-Specific Mutagenesis and Monoclonal Antibodies to Map Regions of CD46 That Interact with Measles Virus H Protein," *Virology* 258(2):314-326.
Jarvis, G.A. et al. (1997). "Expression and Function of Complement Regulatory Proteins CD46, CD55, and CD59 in Prostate Cancer," *J. Allergy Clin. Immunol.* 99(No. 1, Part 2): S215, No. 870.
Jones, P.T. et al. (1986). "Replacing the Complimentarity-Determining Regions in a Human Antibody with Those from a Mouse," *Nature* 321:522-525.
Juhl et al. (1997). "Frequent Expression of Complement Resistance Factors CD46, CD55, and CD59 on Gastrointestinal Cancer Cells Limits the Therapeutic Potential of Monoclonal Antibody 17-1A," *J. Surg. Oncol.* 64:222-230.
Jurianz, K. et al. (1999). "Neutralization of Complement Regulatory Proteins Augments Lysis of Breast Carcinoma Cells Targeted with RhumAb Anti-HER2," *Immunopharmacology* 42(1-3):209-218.
Kinuagasa, N. et al. (1999). "Expression of Membrane Cofactor Protein (MCP, CD46) in Human Liver Diseases," *Br. J. Cancer* 80(11):1820-1825.
Kohler, G. et al. (1975). "Continuous Cultures of Fused Cells Secreting Antibody of Predefined Specificity," *Nature* 256:495-497.
Koretz, K. et al. (1993). "Expression of CD59, A Complement Regulatory Protein and a Second Ligand of the CD2 Molecule, and CD46 in Normal and Neoplastic Colorectal Epithelium," *Br. J. Cancer* 68:926-931.
Liszewski, M.K. et al. (1991). "Membrane Cofactor Protein (MCP or CD46): Newest Member of the Regulators of Complement Activation Gene Cluster," *Annu. Rev. Immunol.* 9:431-455.
Liu, A.Y. (2000). "Differential Expression of Cell Surface Molecules in Prostate Cancer Cells," *Cancer Res.* 60(13):3429-3434.
LoBuglio, A.F. (1989). "Mouse/Human Chimeric Monoclonal Antibody in Man: Kinetics and Immune Response," *Proc. Natl. Acad. Sci. USA* 86:4220-4224.
Lublin, D.M. et al. (1988). "Molecular Cloning and Chromosomal Localization of Human Membrane Cofactor Protein (MCP). Evidence for Inclusion in the Multigene Family of Complement-Regulatory Proteins," *J. Exp. Med.* 168(1):181-194.

Mäenpää, A. et al. (1996). "Expression of Complement Membrane Regulators Membrane Cofactor Protein (CD46), Decay Accelerating Factor (CD55), and Protectin (CD59) in Human Malignant Gliomas," *Am. J. Pathol.* 148(4):1139-1152.

Magyarlaki, T. et al. (1996). "Immunohistochemistry of Complement Response on Human Renal Cell Carcinoma Biopsies," *Tumori* 82(5):473-479.

Maisner et al. (1997). "Membrane Cofactor Protein (CD46) Is a Basolateral Protein That Is Not Endocytosed," *J. Biol. Chem.* 272(33): 20793-20799.

Mangham, D.C. et al. (1999). "A Novel Immunohistochemical Detection System Using Mirror Image Complementary Antibodies (MICA)," *Histopathology* 35(2):129-133.

Mather, J.P. et al. eds.(1998). "Cellular Localization of mRNA and Protein: In Situ Hybridization Histochemistry and In Situ Ligand Binding" Chapter 19 *In Methods in Cell Biology.* Academic Press,Inc., 57:333-351.

Mather, J.P. et al. eds.(1998). "Indirect Immunofluorescence Microscopy in Cultured Cell" Chapter 18 *In Methods in Cell Biology.* Academic Press, Inc., 57:313-332.

Murray, K.P. et al. (2000). "Expression of Complement Regulatory Proteins-CD 35, CD 46, CD 55, and CD 59 in Benign and Malignant Endometrial Tissue," *Gynecol. Oncol.* 76(2):176-182.

Niehans, G.A. et al. (1996). "Human Carcinomas Variably Express the Complement Inhibitory Proteins CD46 (Membrane Cofactor Protein), CD55 (Decay-Accelerating Factor), and CD59 (Protectin)," *American Journal of Pathology* 149(1):129-142.

Noe, K.H. et al. (1999). "Requirements for Measles Virus Induction of Rantes Chemokine in Human Astrocytoma-Derived U373 Cells," *J. Virol.* 73(4):3117-3124.

Ravindranath, N.M. et al. (2000). "Cell-surface Expression of Complement Restriction Factors and Sialyl Lewis Antigens in Oral Carcinoma: Relevance to Chemo-Immunotherapy," *Anticancer Res.* 20(1A):21-26.

Riechmann, L. et al. (Mar. 24, 1988). "Reshaping Human Antibodies for Therapy," *Nature* 332:323-327.

Sakuma, T. et al. (1993). "Levels of Complement Regulatory Molecules in Lung Cancer: Disappearance of D17 Epitope of CD55 in Small-Cell Carcinoma," *Jpn. J. Cancer Res.* 84: 753-759.

Sayama, K. et al. (1992). "Distribution of Complement Regulators (CD46, CD55 and CD59) in Skin Appendages, and in Benign and Malignant Skin Neoplasms," *Br. J. Dermatol.* 127(1):1-4.

Schmitt, C.A. et al. (Jan. 1999). "Expression and Regulation by Interferon-γ of the Membrane-Bound Complement Regulators CD46 (MCP), CD55 (DAF) and CD59 in Gastrointestinal Tumours," *Eur. J. Cancer* 35(1):117-124.

Seto, N. et al. (1996). "Demonstration and Characterization of CD 46, Membrane Cofactor Protein, in Gastric Cancer Tissue," [Article in Japanese] *Nihon Rinsho Meneki Gakkai Kaishi* 19(3):210-216.

Seya, T. (1988). "Structure and Function of a Cell-Associated Complement Regulatory Protein, Membrane Cofactor Protein (MCP)," *Hokkaido Igaku Zasshi* 63(2):259-268.

Seya, T. et al. (1986). "Purification and Characterization of a Membrane Protein (gp45-70) that is a Cofactor for Cleavage of C3b and C4b," *J. Exp. Med.* 163(4):837-855.

Seya, T. et al. (1990). "Quantitative Analysis of Membrane Cofactor Protein (MCP) of Complement: High Expression of MCP on Human Leukemia Cell Lines, Which is Down-Regulated During Cell Differentiation," *J. Immunol.* 145(1):238-245.

Seya, T. et al. (1993). "Membrane Co-Factor Protein (MCP, CD 46) in Seminal Plasma and on Spermatozoa in Normal and 'Sterile' Subjects," *Eur. J. Immunol.* 23:1322-1327.

Shaw, D.R. et al. (1987) "Characterization of a Mouse/Human Chimeric Monoclonal Antibody (17-1A) to A Colon Cancer Tumor-Associated Antigen," *J. Immunol.* 138(12):4534-4538.

Shen, W.-C. et al. (1981). "Cis-Aconityl Spacer Between Daunomycin and Macromolecular Carriers: A Model of PH-Sensitive Linkage Releasing Drug From a Lysosomotropic Conjugate," *Biochem. Biophys. Res. Commun.* 102(3):1048-1054.

Shinoura, N. et al. (1994). "RNA expression of complement regulatory proteins in human brain tumors," *Cancer Lett.* 86(2):143-149.

Simpson, K.L. (1997). "Expression of the Complement Regulatory Proteins Decay Accelerating Factor (DAF, CD55), Membrane Cofactor Protein (MCP, CD46) and CD59 in the Normal Human Uterine Cervix and in Premalignant and Malignant Cervical Disease," *Am. J. Pathol.* 151(5):1455-1467.

Simpson, K.L. et al. (1994). "Differential Expression of Complement Regulatory Proteins Decay-Accelerating Factor (CD55), Membrane Cofactor Protein (CD46) and CD59 During Human Spermatogenesis," *Immunology* 81(3):452-461.

Sparrow, R.L. et al. (1983). "Hu Ly-m5: A Unique Antigen Physically Associated with HLA Molecules," *Hum. Immunol.* 7:1-15.

Stephan, J-P et al. (1999). "Distribution and Function of the Adhesion Molecule BEN during Rat Development," *Dev. Biol.* 212: 264-277.

Stephan, J-P et al. (1999). "Selective Cloning of Cell Surface Proteins Involved in Organ Development: Epithelial Glycoprotein Is Involved in Normal Epithelial Differentiation," *Endocrinology* 140(12): 5841-5854.

Thorsteinsson, L. et al. (1998). "The Complement Regulatory Proteins CD46 and CD59, but not CD55, are Highly Expressed by Glandular Epithelium of Human Breast and Colorectal Tumour Tissues," *APMIS* 106:869-878.

Trouet, A. et al. (1982). "A Covalent Linkage Between Daunorubicin and Proteins that is Stable in Serum and Reversible by Lysosomal Hydrolases, as Required for a Lysosomotropic Drug-Carrier Conjugate: In Vitro and in Vivo Studies," *Proc. Natl. Acad. Sci. USA* 79:626-269.

Varsano, S. et al. (1998). "Cytokines Modulate Expression of Cell-Membrane Complement Inhibitory Proteins in Human Lung Cancer Cell Lines," *Am. J. Respir. Cell. Mol. Biol.* 19:522-529.

Varsano, S. et al. (1998). "Human Lung Cancer Cell Lines Express Cell Membrane Complement Inhibitory Proteins and Are Extremely Resistant to Complement-Mediated Lysis; A Comparison with Normal Human Respiratory Epithelium In Vitro, and an Insight into Mechanism(s) of Resistance," *Clin. Exp. Immunol.* 113:173-182.

Verhoeyen, M. et al. (Mar. 25, 1988). "Reshaping Human Antibodies: Grafting An Antilysozyme Activity," *Science* 239:1534-1536.

Weichenthal, M. et al. (1999). "Expression of Complement Regulator Proteins in Primary and Metastatic Malignant Melanoma," *J. Cutan. Pathol.* 26(5):217-221.

Weiner, L.M. et al. (2001). "Therapeutic Monoclonal Antibodies: General Principles," Chapter 20, Section 5 *In Cancer: Principles and Practice of Oncology.* 6th Edition, J.S. Freeman, Jr. et al. eds., Lippincott Williams & Wilkins: Philadelphia, pp. 495-508.

Winter, G. et al. (1991). "Man-Made Antibodies," *Nature* 349:293-299.

Xu, L.L. et al. (2001). "Quantitative Expression Profile of Androgen-Regulated Genes in Prostate Cancer Cells and Identification of Prostate-Specific Genes," *Int. J. Cancer* 92:322-328.

Yamakawa, M. et al. (1994). "Protection of Thyroid Cancer Cells by Complement-Regulatory Factors," *Cancer* 73(11):2808-2817.

Yang, H.M. et al. (1988). "Pharmacokinetics and Mechanism of Action of a Doxorubicin-Monoclonal Antibody 9.2.27 Conjugate Directed to a Human Melanoma Proteoglycan," *J. Natl. Canc. Inst.* 80(14):1154-1159.

Falini, B. et al. (May 16, 1992). "Response of Refractory Hodgkin's Disease to Monoclonal Anti-CD30 Immunotoxin," *The Lancet* 339:1195-1196.

* cited by examiner

Filled asterix = CD46
Clear asterix = IgG

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Synthetic Construct

<400> SEQUENCE: 1

```
Gly Gly Gly Gly Ser Gly Gly Gly Gly Ser Gly Gly Gly Gly Ser
1               5                  10                  15
```

US 7,744,878 B2

ANTIBODIES THAT BIND TO CANCER-ASSOCIATED ANTIGEN CD46 AND METHODS OF USE THEREOF

CROSS-REFERENCE TO RELATED APPLICATIONS

This application is a continuation of U.S. patent application Ser. No. 10/272,835, filed Oct. 16, 2002, issued as U.S. Pat. No. 7,148,038; which claims the benefit of U.S. provisional patent application Ser. No. 60/329,644, filed Oct. 16, 2001; the disclosures of which are herein incorporated by reference in their entirety.

TECHNICAL FIELD

This invention is in the fields of cancer biology and immunotherapy. More specifically, it concerns the discovery of antibodies that bind to CD46 (membrane cofactor protein), which is present in a variety of human cancers, and methods of diagnosing and/or treating such cancers.

BACKGROUND OF THE INVENTION

Immunotherapy, or the use of antibodies for therapeutic purposes has been used in recent years to treat cancer. Passive immunotherapy involves the use of monoclonal antibodies in cancer treatments. See for example, *Cancer: Principles and Practice of Oncology*, 6th Edition (2001) Chapt. 20 pp. 495-508. These antibodies can have inherent therapeutic biological activity both by direct inhibition of tumor cell growth or survival and by their ability to recruit the natural cell killing activity of the body's immune system. These agents can be administered alone or in conjunction with radiation or chemotherapeutic agents. Rituxan® and Herceptin®, approved for treatment of lymphoma and breast cancer, respectively, are two examples of such therapeutics. Alternatively, antibodies can be used to make antibody conjugates where the antibody is linked to a toxic agent and directs that agent to the tumor by specifically binding to the tumor. Mylotarg® is an example of an approved antibody conjugate used for the treatment of leukemia. Monoclonal antibodies that bind to cancer cells and have potential uses for diagnosis and therapy have been disclosed in publications. See, for example, the following patent applications which disclose, inter alia, some molecular weights of target proteins: U.S. Pat. No. 6,054,561 (200 KD c-erbB-2 (Her2), and other unknown antigens 40-200 KD in size) and U.S. Pat. No. 5,656,444 (50 KD and 55 KD, oncofetal protein). Example of antibodies in clinical trials and/or approved for treatment of solid tumors include: Herceptin® (antigen: 180 kD, HER2/neu), Panorex® (antigen: 40-50 kD, Ep-CAM), HMFG1 (antigen>200 kD, HMW Mucin), C225 (antigens: 150 kD and 170 kD, EGF receptor), Campath® (antigen: 21-28 kD, CD52), and Rituxan® (antigen: 35 kD, CD20).

Another type of immunotherapy is active immunotherapy, or vaccination, wherein the antigen present on a specific cancer evokes the immune response in the patient, i.e., to induce the patient to actively produce antibodies against their own cancer. Active immunization has not been used as often as passive immunotherapy or immunotoxins.

An ideal diagnostic and/or therapeutic antibody would be specific for an antigen present on a large number of cancers, but absent or present only at low levels on any adult tissue. The discovery, characterization, and isolation of a novel antigen which is specifically associated with cancer(s) would be useful in many ways. First, the antigen could be used to make monoclonal antibodies against the antigen. An antibody would ideally have biological activity against cancer cells and be able to recruit the immune system's response to foreign antigens. An antibody could be administered as a therapeutic alone or in combination with current treatments or used to prepare immunoconjugates linked to toxic agents. An antibody with the same specificity but without biological activity when administered alone could also be useful in that an antibody could be used to prepare an immunoconjugate with a radio-isotope, a toxin, or a chemotherapeutic agent or liposome containing a chemotherapeutic agent, with the conjugated form being biologically active by virtue of the antibody directing the toxin to the antigen-containing cells.

One aspect required for the ideal diagnostic and/or therapeutic antibody is the discovery and characterization of an antigen which is associated with a variety of cancers. There are few antigens that are expressed on a number of types of cancer (e.g., "pan-cancer" antigen) that have limited expression on non-cancerous cells. The isolation and purification of such an antigen would be useful for making antibodies (e.g., diagnostic or therapeutic) targeting the antigen. An antibody binding to the "pan-cancer" antigen could be able to target a variety of cancers found in different tissues in contrast to an antibody against an antigen associated with only one specific type of cancer. The antigen would also be useful for drug discovery (e.g., small molecules) and for further characterization of cellular regulation, growth, and differentiation.

Antibodies to CD46 (also known as membrane cofactor protein or MCP), have been reported. See, for example, Sparrow et al. *Hum. Immunol.* 7:1 (1983); Hsi et. al. *Am. J. Reprod. Immunol. Microbiol.* 18:21 (1988); Cho et al. *Clin. Exp. Immunol.* 83:257 (1991); Seya et al. *J. Immunol.* 145:238 (1990). The expression of CD46 has been reported in certain types of cancer, such as breast cancer (Thorseinsson et al. *APMIS* 106:869-78 (1998); Hofman et al. *Breast Cancer Res. Treat.* 32:213-9 (1994)); colon/colorectal cancer (Andrew et al. *Cancer Res.* 50: 5225-30 (1990); Koretz et al. *Br. J. Cancer* 68:926-31 (1993); Juhl et al. *J. Surg. Oncol.* 64:222-30 (1997); Bjorge et al. *Cancer Immunol. Immunother.* 42:185-92 (1996)); lung cancer (Varsano et al. *Clin. Exp. Immunol.* 113:173-82 (1998); Varsano et al. *Am. J. Respir. Cell. Mol. Biol.* 19:522-9 (1998)); ovarian cancer (Bjorge et al. *Int. J. Cancer* 70:14-25 (1997)); renal cancer (Blok et al. *Lab. Invest.* 80:335-44 (2000); Gorter et al. Lab. Invest. 74:1039-49 (1996)); pancreatic cancer (Juhl et al. *J. Surg. Oncol.* 64:222-30 (1997)); and prostate cancer (Jarvis et al. *J. Allergy Clin. Immunol* 99(NO.1, PART 2): S215 (1997); Liu et al. *Cancer Res.* 60: 3429-3434 (2000)); see also, PCT WO 02/18948; PCT WO 01/88537.

All references, publications, and patent applications disclosed herein are hereby incorporated by reference in their entirety.

SUMMARY OF THE INVENTION

The invention disclosed herein concerns antibodies to an antigen, CD46 (also known as membrane cofactor protein), which is present in a variety of human cancers. Accordingly, in one aspect, the invention is an antibody or a polypeptide (which may or may not be an antibody) that binds preferentially to the antigen, hereinafter known as "Ag-PA7" or CD46, where CD46 is approximately 55 kDa +/−10% on a 4-20% Tris-glycine SDS-PAGE (i.e., denaturing gradient) gel.

In another aspect, the invention is an antibody mPA7 that is produced by a host cell (ATCC No. PTA-3706). The epitope on CD46 that mPA7 binds is disulfide bond dependent.

In another aspect, the invention is an antibody or a polypeptide (which may or may not be an antibody) that binds preferentially to the same epitope on CD46 as mPA7 binds preferentially. The epitope on CD46 that the antibody or the polypeptide binds is disulfide bond dependent.

In another aspect, the invention is an antibody comprising a fragment or a region of the antibody mPA7. In one embodiment, the fragment is a light chain of the antibody mPA7. In another embodiment, the fragment is a heavy chain of the antibody mPA7. In yet another embodiment, the fragment contains one or more variable regions from a light chain and/or a heavy chain of the antibody mPA7. In yet another embodiment, the fragment contains one or more complementarity determining regions (CDRs) from a light chain and/or a heavy chain of the antibody mPA7.

In another aspect, the invention provides polypeptides (which may or may not be antibodies) comprising any of the following: a) one or more CDRs; b) three CDRs from the light chain; c) three CDRs from the heavy chain; d) three CDRs from the light chain and three CDRs from the heavy chain; e) the light chain variable region; f) the heavy chain variable region of the antibody mPA7.

In another aspect, the invention is a humanized antibody derived from mPA7. In some embodiments, the humanized antibody comprises one or more CDRs of the antibody mPA7. In another aspect, the invention provides a humanized antibody that binds to the same epitope(s) as antibody mPA7. The epitope that the humanized antibody binds is disulfide bond dependent. Generally, a humanized antibody of the invention comprises one or more (one, two, three, four, five, six) CDRs which are the same and/or derived from the CDR(s) of antibody mPA7. In other aspect, the invention provides a human antibody which binds to the same epitope(s) on CD46 as antibody mPA7. The epitope that the human antibody binds is disulfide bond dependent.

In anther aspect, the invention is a chimeric antibody comprising variable regions derived from variable regions of a heavy chain and a light chain of antibody mPA7 and constant regions derived from constant regions of a heavy chain and a light chain of a human antibody.

In yet another aspect, the invention is a host cell (ATCC No. PTA-3706) or progeny thereof which produces monoclonal antibody mPA7.

In another aspect, the invention is an isolated polynucleotide that encodes for antibody mPA7 that is produced by a host cell with a deposit number of ATCC No. PTA-3706 or progeny thereof. In another aspect, the invention provides polynucleotides encoding any of the antibodies (including antibody fragments) as well as any other polypeptides described herein.

In another aspect, the invention is a complex of CD46 bound by any of the antibody or polypeptides described herein. In some embodiments, the CD46 is present on breast, colon, lung, ovarian, pancreatic, prostate, or kidney cancer cells. In one embodiment, the invention is a complex of CD46 on prostate cancer cells bound by any of the antibody or polypeptides described herein. In some embodiments, the invention is a complex of CD46 bound by antibody mPA7 or an antibody that binds preferentially to the epitope that antibody mPA7 binds preferentially. This epitope is disulfide bond dependent. In one embodiment, antibody mPA7 or any antibody that binds preferentially to the epitope that antibody mPA7 binds preferentially is linked to a therapeutic agent (such as a toxin).

In another aspect, the invention is a complex of a cancer cell expressing CD46 bound by any of the antibody or polypeptides described herein. In some embodiments, the cancer cell is breast, colon, lung, ovarian, pancreatic, prostate, or kidney cancer cell. In some embodiments, the antibody is mPA7 or any antibody that binds preferentially to the epitope that antibody mPA7 binds preferentially. This epitope is disulfide bond dependent. In some embodiments, antibody mPA7 or any antibody that binds preferentially to the epitope that antibody mPA7 binds preferentially is linked to a therapeutic agent (such as a toxin).

In another aspect, the invention is a complex of an epitope that mPA7 preferentially binds bound by any of the antibody or polypeptides described herein. In some embodiments, the epitope is on breast, colon, lung, ovarian, pancreatic, prostate, or kidney cancer cell. In some embodiments, the antibody is mPA7 or any antibody that binds preferentially to the epitope that antibody mPA7 binds preferentially. This epitope is disulfide bond dependent. In some embodiments, antibody mPA7 or any antibody that binds preferentially to the epitope that antibody mPA7 binds preferentially is linked to a therapeutic agent (such as a toxin).

In another aspect, the invention is a pharmaceutical composition comprising any of the polypeptides (including any of the antibodies such as antibody mPA7) or polynucleotides described herein, such as pharmaceutical compositions comprising the antibody mPA7, the antibody mPA7 linked to a therapeutic agent, an antibody comprising a fragment of the antibody mPA7, a humanized antibody of the antibody mPA7, a chimeric antibody comprising variable regions derived from variable regions of the antibody mPA7 and constant regions derived from constant regions of a human antibody, or a human antibody with one or more properties of the antibody mPA7, and a pharmaceutically acceptable excipient.

In yet another aspect, the invention is a method of generating a monoclonal antibody having greater affinity to cancerous cells than non-cancerous cells comprising the steps of: (a) immunizing a host mammal with intact human fetal pancreatic epithelial progenitor (hPED) cells; (b) obtaining lymphocytes from the mammal; (c) fusing lymphocytes with a myeloma cell line to produce a hybridoma; (d) culturing the hybridoma under conditions sufficient to produce monoclonal antibodies; (e) selecting antibodies that preferentially bind to hPED cells; and (f) selecting from the antibodies obtained from step (e) an antibody that binds to cancerous cells with greater affinity than non-cancerous cells. The method may further comprising the steps of selecting the antibody which binds to cancerous cells or cancerous cell lines but does not bind to non-cancerous cells or cell lines.

In another aspect, the invention is a method of generating antibody mPA7 comprising culturing a host cell (ATCC No. PTA-3706) or progeny thereof under conditions that allow production of antibody mPA7, and purifying the antibody mPA7.

In another aspect, the invention provides methods of generating any of the antibodies (or polypeptides) described herein by expressing one or more polynucleotides encoding the antibody (which may be separately expressed as a single light or heavy chain, or both a light and a heavy chain are expressed from one vector) in a suitable cell, generally followed by recovering and/or isolating the antibody or polypeptides of interest.

In another aspect, the invention is a method of diagnosing cancer in an individual by detecting CD46 on cells from the individual using the antibody mPA7 or any CD46 binding moiety (polypeptides, including, but not limited to, various antibodies and antibody derivatives) described herein. In some embodiments, the cancer is breast, colon, lung, ovarian, pancreatic, prostate, and renal. In some embodiments, the method is detecting the level of CD46 from cells. The presence of CD46 is detected by detecting a complex between CD46 and a CD46 binding moiety. The term "detection" as used herein include qualitative and/or quantitative detection (measuring levels) with or without reference to a control.

In another aspect, the invention is a method of treating cancer by administering an effective amount of a composition comprising the antibody mPA7, or any of the antibodies (including polypeptides) or polynucleotides embodiments described herein, including but not limited to the antibody mPA7 associated with a therapeutic agent, an antibody comprising a fragment or a region of the antibody mPA7, a humanized antibody (generally, but not necessarily, comprising one or more CDRs of the antibody mPA7), a chimeric antibody comprising variable regions derived from variable regions of the antibody mPA7 and constant regions derived from constant regions of a human antibody, or a human antibody with one or more properties of the antibody mPA7, sufficient to reduce growth of cancerous cells. In some embodiments, the cancer is breast, colon, lung, ovarian, pancreatic, prostate, or renal.

In another aspect, the invention is a method of inhibiting growth and/or proliferation of cancerous cells in an individual by administering to the individual an effective amount of a composition comprising the antibody mPA7, or any of the antibodies (including polypeptides) or polynucleotides embodiments described herein, including but not limited to the antibody mPA7 associated with a therapeutic agent, an antibody comprising a fragment or a region of the antibody mPA7, a humanized antibody (generally, but not necessarily, comprising one or more CDRs of the antibody mPA7), a chimeric antibody comprising variable regions derived from variable regions of the antibody mPA7 and constant regions derived from constant regions of a human antibody, or a human antibody with one or more properties of the antibody mPA7, sufficient to reduce growth of cancerous cells. In some embodiments, the cancer is breast, colon, lung, ovarian, pancreatic, prostate, or renal.

In another aspect, the invention is a method of delaying development of metastasis in an individual with cancer by administering an effective amount of a composition comprising the antibody mPA7, or any of the antibodies (including polypeptides) or polynucleotides embodiments described herein, including but not limited to the antibody mPA7 associated with a therapeutic agent, an antibody comprising a fragment or a region of the antibody mPA7, or a humanized antibody (generally, but not necessarily, comprising one or more CDRs of the antibody mPA7), a chimeric antibody comprising variable regions derived from variable regions of the antibody mPA7 and constant regions derived from constant regions of a human antibody, or a human antibody with one or more properties of the antibody mPA7, sufficient to reduce growth of cancerous cells. In some embodiments, the cancer is breast, colon, lung, ovarian, pancreatic, prostate, or renal.

In another aspect, the invention is a method of delivering a therapeutic agent (such as a toxin, or a radioactive molecule) to cancerous cells in an individual by administering to the individual an effective amount of a CD46 binding antibody or any CD46 binding moiety (polypeptides, including but not limited to antibodies or antibody derivatives) described herein that are linked to a therapeutic agent (such as a toxin or a radioactive molecule). The CD46 binding moiety includes, but not limited to the antibody mPA7, an antibody comprising a fragment or a region of the antibody mPA7, or a humanized antibody (generally, but not necessarily, comprising one or more CDRs of the antibody mPA7), a chimeric antibody comprising variable regions derived from variable regions of the antibody mPA7 and constant regions derived from constant regions of a human antibody, or a human antibody with one or more properties of the antibody mPA7. In some embodiments, the cancerous cells are from breast, colon, lung, ovarian, pancreatic, prostate, or renal cancer. In another embodiment, the therapeutic agent (such as a toxin or a radioactive molecule) is delivered into the cancerous cells (is internalized). In another embodiment the therapeutic agent is delivered into prostate, ovarian, breast, or colon cancer cells. Accordingly, the invention provides methods of inhibiting growth and/or proliferation of prostate, ovarian, breast, or colon cancer cells such that the therapeutic agent is delivered into those cancer cells. In another embodiment, the therapeutic agent is saporin.

In another aspects, the invention provides kits comprising any one or more of the compositions described herein. These kits, generally in suitable packaging and provided with appropriate instructions, are useful for any of the methods described herein.

DETAILED DESCRIPTION OF THE INVENTION

Figure 1:
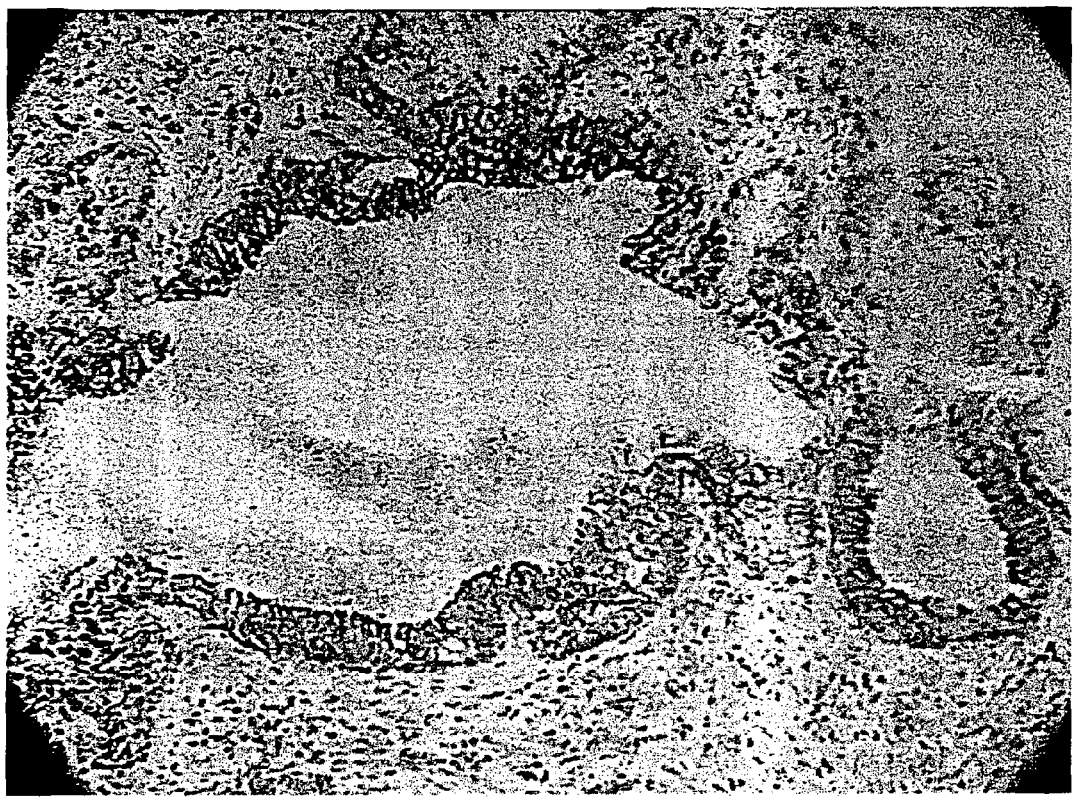
FIG. 1 is a photograph showing mPA7 staining human lung carcinoma.

The invention disclosed herein provides antibodies and polypeptides which bind to an antigen, CD46 and methods of making and using these antibodies and polypeptides which bind to CD46. CD46 has been shown to be present and its expression is increased in a variety of human cancers. An antibody mPA7, which binds preferentially to a CD46 epitope which is disulfide bond dependent, has been found to suppress growth of prostate cancer cells in vitro and in an in vivo model, and has displayed an ability to internalize a therapeutic agent in cancer cells.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989) Cold Spring Harbor Press; *Oligonucleotide Synthesis* (M. J. Gait, ed., 1984); *Methods in Molecular Biology, Humana Press; Cell Biology: A Laboratory Notebook* (J. E. Cellis, ed., 1998) Academic Press; *Animal Cell Culture* (R. I. Freshney, ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Methods in Enzymology* (Academic Press, Inc.); *Handbook of Experimental Immunology* (D. M. Weir and C. C. Blackwell, eds.);

*Gene Transfer Vectors for Mammalian Cells* (J. M. Miller and M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: a practical approach* (D. Catty., ed., IRL Press, 1988-1989); *Monoclonal antibodies: a practical approach* (P. Shepherd and C. Dean, eds., Oxford University Press, 2000); *Using antibodies: a laboratory manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

Definitions

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, fusion proteins comprising an antibody portion, humanized antibodies, chimeric antibodies, and any other modified configuration of the immunoglobulin molecule that comprises an antigen recognition site of the required specificity.

A "monoclonal antibody" refers to a homogeneous antibody population wherein the monoclonal antibody is comprised of amino acids (naturally occurring and non-naturally occurring) that are involved in the selective binding of an antigen. Monoclonal antibodies are highly specific, being directed against a single antigenic site. The term "monoclonal antibody" encompasses not only intact monoclonal antibodies and full-length monoclonal antibodies, but also fragments thereof (such as Fab, Fab', F(ab')$_2$, Fv), single chain (ScFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.).

"Humanized" antibodies refer to a molecule having an antigen binding site that is substantially derived from an immunoglobulin from a non-human species and the remaining immunoglobulin structure of the molecule based upon the structure and/or sequence of a human immunoglobulin. The antigen binding site may comprise either complete variable domains fused onto constant domains or only the complementarity determining regions (CDRs) grafted onto appropriate framework regions in the variable domains. Antigen binding sites may be wild type or modified by one or more amino acid substitutions, e.g., modified to resemble human immunoglobulin more closely. Some forms of humanized antibodies preserve all CDR sequences (for example, a humanized mouse antibody which contains all six CDRs from the mouse antibodies). Other forms of humanized antibodies have one or more CDRs (one, two, three, four, five, six) which are altered with respect to the original antibody, which are also termed one or more CDRs "derived from" one or more CDRs from mPA7.

"Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. Typically, in these chimeric antibodies, the variable region of both light and heavy chains mimics the variable regions of antibodies derived from one species of mammals, while the constant portions are homologous to the sequences in antibodies derived from another. One clear advantage to such chimeric forms is that, for example, the variable regions can conveniently be derived from presently known sources using readily available hybridomas or B cells from non human host organisms in combination with constant regions derived from, for example, human cell preparations. While the variable region has the advantage of ease of preparation, and the specificity is not affected by its source, the constant region being human, is less likely to elicit an immune response from a human subject when the antibodies are injected than would the constant region from a non-human source. However, the definition is not limited to this particular example.

An epitope that "specifically binds" or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a CD46 epitope is an antibody that binds this CD46 epitope with greater affinity, avidity, more readily, and/or with greater duration than it binds to other CD46 epitopes or non-CD46 epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

As used herein, the terms "mPA7", "antibody mPA7" and "monoclonal antibody mPA7" are used interchangeably to refer to immunoglobulin produced by a host cell with a deposit number of ATCC No. PTA-3706 or progeny thereof. The generation and characterization of mPA7 is described in Examples. Different biological functions are associated with mPA7, including, but not limited to, ability to bind to CD46; ability to preferentially bind to a CD46 epitope which is disulfide bond dependent; ability to inhibit growth of cancerous cells expressing CD46, such as prostate cancer cells; ability to delay development of metastasis in an individual with cancerous cells expressing CD46; ability to deliver a therapeutic agent, such as a toxin or a radioactive compound to cancerous cells expressing CD46; ability to deliver a therapeutic agent into cancerous cells expressing CD46, such as prostate, ovarian, breast, or colon cancer cells; ability to inhibit growth and/or proliferation of vascular endothelial cells (such as venous endothelial cells); ability to deliver a therapeutic agent into proliferating vascular endothelial cells expressing CD46 (such as venous endothelial cells); ability to inhibit angiogenesis. As discussed herein, polypeptides (including antibodies) of the invention may have any one or more of these characteristics.

A "mPA7 equivalent antibody" or "mPA7 equivalent polypeptide" refers to an antibody or a polypeptide having one or more biological functions associated with mPA7.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

A "variable region" of an antibody refers to the variable region of the antibody light chain or the variable region of the antibody heavy chain, either alone or in combination.

A "constant region" of an antibody refers to the constant region of the antibody light chain or the constant region of the antibody heavy chain, either alone or in combination.

As used herein, "substantially pure" refers to material which is at least 50% pure (i.e., free from contaminants), more preferably at least 90% pure, more preferably at least 95% pure, more preferably at least 98% pure, more preferably at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

An "effective amount" of drug, compound, or pharmaceutical composition is an amount sufficient to effect beneficial or desired results including clinical results such as shrinking the size of the tumor, retardation of cancerous cell growth, decreasing one or more symptoms resulting from the disease, increasing the quality of life of those suffering from the disease, decreasing the dose of other medications required to treat the disease, enhancing effect of another medication such as via targeting and/or internalization, delaying the progression of the disease, and/or prolonging survival of patients. An effective amount can be administered in one or more administrations. For purposes of this invention, an effective amount of drug, compound, or pharmaceutical composition is an amount sufficient to reduce the proliferation of (or destroy) neoplastic cells and/or to reduce and/or delay the development, or growth, of metastases of neoplastic cells, either directly or indirectly. As is understood in the cancer clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, "treatment" or "treating" is an approach for obtaining beneficial or desired results including and preferably clinical results. For purposes of this invention, beneficial or desired clinical results include, but are not limited to, one or more of the following: reducing the proliferation of (or destroying) neoplastic cells, reducing metastasis of neoplastic cells found in cancers, shrinking the size of the tumor, decreasing symptoms resulting from the disease, increasing the quality of life of those suffering from the disease, decreasing the dose of other medications required to treat the disease, delaying the progression of the disease, and/or prolonging survival of patients.

As used herein, "delaying development of metastasis" means to defer, hinder, slow, retard, stabilize, and/or postpone development of metastasis. This delay can be of varying lengths of time, depending on the history of the cancer and/or individual being treated. As is evident to one skilled in the art, a sufficient or significant delay can, in effect, encompass prevention, in that the individual does not develop the metastasis.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples.

An "individual" is a vertebrate, preferably a mammal, more preferably a human. Mammals include, but are not limited to, farm animals, sport animals, pets (such as cats, dogs, horses), primates, mice and rats.

"Toxin" or "cytotoxin" refers to any substance which effects an adverse response within a cell. For example, a toxin directed to a cancerous cell would have an adverse, sometimes deleterious effect, on the cancerous cell.

As used herein, "agent" refers to a biological, pharmaceutical, or chemical compound. Non-limiting examples include simple or complex organic or inorganic molecule, a peptide, a protein, an oligonucleotide, an antibody, an antibody derivative, or antibody fragment. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

As used herein, a "therapeutic agent" means any agent useful for therapy (here, generally in the cancer context) including anti-tumor drugs, toxins or cytotoxins, cytotoxin agents, and radioactive agents.

"Active immune response" refers to the development of, and on-going production of, antibodies in vivo directed against an antigen, in response to the administration of the antigen, or DNA vectors coding for that antigen, to the host mammal by intravenous, intramuscular, subcutaneous, or other mode of administration with or without an adjuvant. Active immune response can also include other aspects of the immune response, such as a cellular immune response.

Compositions and Methods of Making the Compositions

This invention encompasses compositions, including pharmaceutical compositions, comprising antibodies, polypeptides and proteins that bind to CD46 (also known as membrane cofactor protein, or MCP), and polynucleotides comprising sequences encoding antibodies, polypeptides and proteins that bind to CD46. As used herein, compositions comprise one or more antibodies, polypeptides and/or proteins that bind to CD46, and/or one or more polynucleotides comprising sequences encoding one or more antibodies, polypeptides and proteins that bind to CD46. These compositions may further comprise suitable excipients, such as pharmaceutically acceptable excipients including buffers, which are well known in the art.

The antibodies, polypeptides and proteins of this invention are further identified and characterized by any (one or more) of the following criteria: (a) ability to bind to CD46; (b) ability to preferentially bind to the CD46 epitope to which mPA7 preferentially binds, which is disulfide bond dependent; (c) ability to bind CD46 on cancer cells, such as breast, colon, lung, ovarian, pancreatic, prostate, or renal cancer cells; (d) ability to inhibit growth and/or proliferation of cancerous cells expressing CD46, such as prostate, lung, breast, ovarian, pancreatic, colon, or renal cancer cells; (e) ability to delay development of metastasis in an individual with cancerous cells expressing CD46; (f) ability to deliver a therapeutic agent, such as a toxin or a radioactive compound to cancerous cells expressing CD46; (g) ability to deliver a therapeutic agent into cancerous cells expressing CD46, such as prostate, ovarian, breast, or colon cancer cells; (h) ability to inhibit growth and/or proliferation of vescular endothelial cells (such as venous endothelial cells); (i) ability to deliver a therapeutic agent into proliferating vescular endothelial cells expressing CD46 (such as venous endothelial cells); (j) ability to inhibit angiogenesis.

In some embodiments, the antibody of the invention is an antibody mPA7 that is produced by a host cell with a deposit number of ATCC No. PTA-3706 or progeny thereof. The present invention also encompasses various formulations of mPA7 and equivalent antibodies or polypeptide fragments (e.g., Fab, Fab', F(ab')$_2$, Fv, Fc, etc.), chimeric antibodies, single chain (ScFv), mutants thereof, fusion proteins comprising an antibody portion, humanized antibodies, and any other modified configuration of mPA7 that comprises an antigen (Ag-PA7; CD46), recognition site of the required specificity. The invention also provides human antibodies displaying one or more of the biological characteristics of mPA7. The equivalent antibodies of mPA7 (including humanized antibodies and human antibodies), polypeptide fragments of mPA7, and polypeptides comprising any of these fragments are identified and characterized by any (one or more) of the ten criteria described above.

In some embodiments, the antibodies, polypeptides and proteins of the invention that bind to CD46 are antibodies, polypeptides and proteins that preferentially bind to the same epitope on CD46 as the antibody mPA7 preferentially binds.

Accordingly, the invention provides any of the following (or compositions, including pharmaceutical compositions), comprising any of the following:

(a) antibody mPA7 produced by the host cell with a deposit number of ATCC No. PTA-3706 or its progeny; (b) a humanized form of antibody mPA7; (c) an antibody comprising one or more of the light chain and/or heavy chain variable regions of antibody mPA7; (d) a chimeric antibody comprising variable regions homologous or derived from variable regions of a heavy chain and a light chain of antibody mPA7, and constant regions homologous or derived from constant regions of a heavy chain and a light chain of a human antibody; (e) an antibody comprising one or more of the light chain and/or heavy chain CDRs (at least one, two, three, four, five, or six) of mPA7; (f) an antibody comprising a heavy and/or a light chain of mPA7; (g) a human antibody that is equivalent to mPA7. A humanized form of the antibody may or may not have CDRs identical to mPA7, or antibody produced by the host cell with a deposit number of ATCC No. PTA-3706. Determination of CDR regions is well within the skill of the art. In some embodiments, the invention provides an antibody which comprises at least one CDR that is substantially homologous to at least one CDR, at least two, at least three, at least four, at least 5 CDRs of mPA7 (or, in some embodiments substantially homologous to all 6 CDRs of mPA7, or derived from mPA7), or antibody produced by the host cell with a deposit number of ATCC No. PTA-3706. Other embodiments include antibodies which have at least two, three, four, five, or six CDR(s) that are substantially homologous to at least two, three, four, five or six CDRs of mPA7 or derived from mPA7, or antibody produced by the host cell with a deposit number of ATCC No. PTA-3706. It is understood that, for purposes of this invention, binding specificity and/or overall activity (which may be in terms of reducing the growth and/or proliferation of cancerous cells, inducing apoptotic cell death in the cancer cell, delaying the development of metastasis, and/or treating palliatively) is generally retained, although the extent of activity may vary compared to mPA7 (may be greater or lesser). The invention also provides methods of making any of these antibodies. Methods of making antibodies are known in the art and are described herein.

The invention also provides polypeptides comprising an amino acid sequence of the antibodies of the invention, such as mPA7. In some embodiments, the polypeptide comprises one or more of the light chain and/or heavy chain variable regions of the antibody mPA7. In some embodiments, the polypeptide comprises one or more of the light chain and/or heavy chain CDRs of mPA7. In some embodiments, the polypeptide comprises three CDRs of the light chain and/or heavy chain of mPA7. In some embodiments, the polypeptide comprises an amino acid sequence of mPA7 that has any of the following: at least 5 contiguous amino acids of a sequence of mPA7, at least 8 contiguous amino acids, at least about 10 contiguous amino acids, at least about 15 contiguous amino acids, at least about 20 contiguous amino acids, at least about 25 contiguous amino acids, at least about 30 contiguous amino acids, wherein at least 3 of the amino acids are from a variable region of mPA7. In one embodiment, the variable region is from a light chain of mPA7. In another embodiment, the variable region is from a heavy chain of mPA7. In another embodiment, the 5 (or more) contiguous amino acids are from a complementarity determining region (CDR) of mPA7.

Antibodies may be polyclonal (e.g., not homogeneous) or monoclonal. Methods of making monoclonal antibodies are known in the art. One method which may be employed is the method of Kohler and Milstein, Nature 256:495-497 (1975) or a modification thereof. In general, a mouse or rat is used for immunization but other animals may also be used. The immunogen can be, but is not limited to, primary cells, cultured cell lines, cancerous cells, nucleic acids, tissue, or peptides. In one embodiment, human fetal pancreatic epithelial cells (hPED) are used. Methods for isolating and culturing human pancreatic epithelial progenitor cells (hereinafter known as "hPED") are detailed in the Examples section. Cells used for immunogen, for example, hPED cells, may be cultured for a period of time (at least 24 hours) prior to their use as an immunogen. Cells (e.g., hPED cells) may be used as immunogens by themselves or in combination with a non-denaturing adjuvant, such as Ribi. In general, cells (e.g., hPED cells) should be kept intact and preferably viable when used as immunogens. Intact cells may allow antigens to be detected better than ruptured cells. Use of denaturing or harsh adjuvants, e.g., Freud's adjuvant, may rupture the hPED cells and therefore is discouraged. In another embodiment, full length CD46 or any fragments of CD46, or CD46 expressing cancer cells are used as immunogen. The immunogen may be administered multiple times at periodic intervals such as, bi-weekly, or weekly, or may be administered in such a way as to maintain viability in the animal (e.g., in a tissue recombinant).

To monitor the antibody response, a small biological sample (e.g. blood) may be obtained from the animal and tested for antibody titer against the immunogen. The spleen and/or several large lymph nodes can be removed and dissociated into single cells. If desired, the spleen cells may be screened (after removal of non-specifically adherent cells) by applying a cell suspension to a plate or to a well coated with the antigen. B-cells, expressing membrane-bound immunoglobulin specific for the antigen, will bind to the plate, and are not rinsed away with the rest of the suspension. Resulting B-cells, or all dissociated spleen cells, can then be fused with myeloma cells (e.g., X63-Ag8.653 and those from the Salk Institute, Cell Distribution Center, San Diego, Calif.). Polyethylene glycol (PEG) may be used to fuse spleen or lymphocytes with myeloma cells to form a hybridoma. The hybridoma is then cultured in a selective medium (e.g., hypoxanthine, aminopterin, thymidine medium, otherwise known as "HAT medium"). The resulting hybridomas are then plated by limiting dilution, and are assayed for the production of antibodies which bind specifically to the immunogen (e.g., surface of the hPED cells, surface of cancer cell lines, fetal ovary sections, CD46, etc.) using FACS or immunohistochemistry (IHC screening). The selected monoclonal antibody-secreting hybridomas are then cultured either in vitro (e.g., in tissue culture bottles or hollow fiber reactors), or in vivo (e.g., as ascites in mice). Examples further detail the methods utilized to obtain, screen, and characterize an antibody mPA7, which binds to Ag-PA7 (CD46). Methods of culturing hybridoma under conditions to generate the antibody mPA7, and purifying the antibody are known in the art and are further detailed in Examples 2 and 3.

Monoclonal antibody-secreting hybridomas described above can be selected for producing antibodies that bind preferentially to the epitope on CD46 that the antibody mPA7 preferentially binds. Methods of selecting such antibody are known in the art. For example, binding competition assays can be used to determine whether an antibody binds to the same epitope as mPA7. An antibody's competition with mPA7 for binding to CD46 indicates that the antibody binds preferentially to the epitope that mPA7 binds. Binding competition assays are well known in the art. Another indication that an antibody preferentially binds to the epitope that mPA7 preferentially binds is that the epitope that that antibody binds is also disulfide bond dependent. Polypeptides that bind preferentially to the epitope on CD46 that the antibody mPA7 binds preferentially can also be tested and identified using similar methods.

As another alternative to the cell fusion technique, EBV immortalized B cells may be used to produce monoclonal antibodies of the subject invention. The hybridomas are expanded and subcloned, if desired, and supernatants are assayed for anti-immunogen activity by conventional assay procedures (e.g., FACS, IHC, radioimmunoassay, enzyme immunoassay, fluorescence immunoassay, etc.).

In another alternative, the antibodies can be made recombinantly. Methods for making recombinant antibodies are well-known in the art. Monoclonal antibody mPA7 and any other equivalent antibodies can be sequenced and produced recombinantly in vitro. In one embodiment, mPA7 is sequenced and the polynucleotide sequence is then cloned into a vector for expression or propagation. The sequence encoding the antibody of interest may be maintained in a vector in a host cell and the host cell can then be expanded and frozen for future use. In another alternative, antibodies may be made recombinantly by phage display technology. See, for example, U.S. Pat. Nos. 5,565,332; 5,580,717; 5,733,743; 6,265,150; and Winter et al., Annu. Rev. Immunol. (1994) 12:433-455.

In another alternative, the antibody mPA7 or any other antibodies or protein of interest may be subjected to sequencing by Edman degradation, which is well-known to those of skill in the art. The peptide information generated from mass spectrometry or Edman degradation can be used to design probes or primers that are used to clone the protein of interest.

An alternative method of cloning the protein of interest is by "panning" using CD46 for cells expressing the antibody or protein of interest. The "panning" procedure is conducted by obtaining a cDNA library from tissues or cells that express the antibody or protein of interest, over-expressing the cDNAs in a second cell type, and screening the transfected cells of the second cell type for a specific binding to CD46. Detailed descriptions of the methods used in cloning mammalian genes coding for cell surface proteins by "panning" can be found in the art. See, for example, Aruffo, A. and Seed, B. *Proc. Natl. Acad. Sci. USA,* 84, 8573-8577 (1987) and Stephan, J. et al., *Endocrinology* 140: 5841-5854 (1999).

cDNAs can be obtained by reverse transcribing the mRNAs from a particular cell type according to standard methods in the art. Specifically, mRNA can be isolated using various lytic enzymes or chemical solutions according to the procedures set forth in Sambrook, et al. supra or extracted by commercially available nucleic-acid-binding resins following the accompanying instructions provided by manufacturers (e.g., Qiagen, Invitrogen, Promega). The synthesized cDNAs are then introduced into an expression vector to produce the antibody or protein of interest in cells of a second type. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, and cosmids.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. Preferably, the host cells express the cDNAs at a level of about 5 fold higher, more preferably 10 fold higher, even more preferably 20 fold higher than that of the corresponding endogenous antibody or protein of interest, if present, in the host cells. Screening the host cells for a specific binding to CD46 is effected by an immunoassay or FACS. A cell overexpressed the antibody or protein of interest can be identified.

The invention includes polypeptides comprising an amino acid sequence of the antibodies of this invention, such as mPA7. The polypeptides of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, a mPA7 polypeptide could be produced by an automated polypeptide synthesizer employing the solid phase method.

The invention also encompasses single chain variable region fragments ("scFv") of antibodies of this invention, such as mPA7. Single chain variable region fragments are made by linking light and/or heavy chain variable regions by using a short linking peptide. Bird et al. (1988) *Science* 242: 423-426. An example of a linking peptide is (GGGGS)$_3$ (SEQ ID NO:1), which bridges approximately 3.5 nm between the carboxy terminus of one variable region and the amino terminus of the other variable region. Linkers of other sequences have been designed and used. Bird et al. (1988). Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The invention includes modifications to antibodies, such as antibody mPA7, including functionally equivalent antibodies and polypeptides of mPA7 which do not significantly affect their properties and variants which have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs. Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tryosine. These polypeptides also include glycosylated and nonglycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the variable region. Changes in the variable region can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified mPA7 polypeptides are made using established procedures in the art and can be screened using standard assays known in the art, some of which are described below and in the Examples.

The invention also encompasses fusion proteins comprising one or more fragments or regions from the antibodies of this invention, such as mPA7. In one embodiment, a fusion polypeptide is provided that comprises at least 10 contiguous amino acids of variable light chain region and at least 10 amino acids of variable heavy chain region. In another embodiment, the fusion polypeptide contains a heterologous immunoglobulin constant region. In another embodiment, the fusion polypeptide contains a light chain variable region and a heavy chain variable region of mPA7. For purposes of this invention, a mPA7 fusion protein contains one or more mPA7 polypeptides and another amino acid sequence to which it is not attached in the native molecule, for example, a heterologous sequence or a homologous sequence from another region. A mPA7 polypeptide can be created by methods known in the art, for example, synthetically or recombinantly.

In another embodiment, mPA7 chimeras are provided in which the heavy and/or light chains are fusion proteins. In some embodiments, the constant domain of the chains is from one particular species and/or class, and the variable domains are from a different species and/or class. For instance, a chimeric antibody (in some embodiments) is one in which the constant regions are derived from human origin, and the variable regions are homologous or derived from mPA7 (i.e., murine). Also embodied within the invention is an antibody with a humanized variable region, in which (in some embodiments) the CDR regions comprise mPA7 amino acid sequences, while the framework regions are derived from human sequences. Other forms of humanized antibodies are known in the art and described herein. Also embodied are functional fragments of chimeras. An example is a humanized Fab fragment, which contains a human hinge region, a human first constant region, a human kappa light or heavy chain constant region, and the variable region of light and/or heavy chain from mPA7. The humanized mPA7 Fab fragments can in turn be made to form Fab dimers. Typically, the mPA7 fusion proteins and mPA7 chimeras of this invention are made by preparing an expressing a polynucleotide encoding them using recombinant methods described herein, although they may also be prepared by other means known in the art, including, for example, chemical synthesis. See, for example, U.S. Pat. Nos. 5,807,715; 4,816,567; and 6,331,415.

The invention also encompasses humanized antibodies. The polynucleotide sequence of an antibody, such as mPA7 or other equivalent antibodies may be used for genetic manipulation to generate a "humanized" antibody, or to improve the affinity, or other characteristics of the antibody. The general principle in humanizing an antibody involves retaining the basic sequence of the antigen-binding portion of the antibody, while swapping the non-human remainder of the antibody with human antibody sequences. There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. For example, the constant region may be engineered to more resemble human constant regions to avoid immune response if the antibody is used in clinical trials and treatments in humans. See, for example, U.S. Pat. Nos. 5,997,867 and 5,866,692.

A number of "humanized" antibody molecules comprising an antigen-binding site derived from a non-human immunoglobulin have been described, including chimeric antibodies having rodent V regions and their associated complementarity determining regions (CDRs) fused to human constant domains. See, for example, Winter et al. *Nature* 349:293-299 (1991); Lobuglio et al. *Proc. Nat. Acad. Sci. USA* 86:4220-4224 (1989); Shaw et al. *J Immunol.* 138:4534-4538 (1987); and Brown et al. *Cancer Res.* 47:3577-3583 (1987). Other references describe rodent CDRs grafted into a human supporting framework region (FR) prior to fusion with an appropriate human antibody constant domain. See, for example, Riechmann et al. *Nature* 332:323-327 (1988); Verhoeyen et al. *Science* 239:1534-1536 (1988); and Jones et al. *Nature* 321:522-525 (1986). Another reference describes rodent CDRs supported by recombinantly veneered rodent framework regions. See, for example, European Patent Publication No. 519,596. These "humanized" molecules are designed to minimize unwanted immunological response toward rodent antihuman antibody molecules which limits the duration and effectiveness of therapeutic applications of those moieties in human recipients. Other methods of humanizing antibodies that may also be utilized are disclosed by Daugherty et al., *Nucl. Acids Res.*, 19:2471-2476 (1991) and in U.S. Pat. Nos. 6,180,377; 6,054,297; 5,997,867; 5,866,692; 6,210,671; 6,350,861; and PCT WO 01/27160.

In yet another alternative, fully human antibodies may be obtained by using commercially available mice which have been engineered to express specific human immunoglobulin proteins. Transgenic animals which are designed to produce a more desirable (e.g., fully human antibodies) or more robust immune response may also be used for generation of humanized or human antibodies. Examples of such technology are Xenomouse® from Abgenix, Inc. (Fremont, Calif.) and HuMAb-Mouse® and TC Mouse™ from Medarex, Inc. (Princeton, N.J.).

This invention also provides compositions comprising mPA7 or mPA7 equivalent antibodies or polypeptides conjugated (for example, linked) to a therapeutic agent, such as a radioactive molecule, a toxin (e.g., calicheamicin), or a chemotherapeutic molecule, or to liposomes or other vesicles containing chemotherapeutic compounds. The compositions, when administered to an individual, can target these agents to a cancer cell expressing CD46 recognized by the antibody or polypeptide(s) and thus can, for example, eliminate cancerous cells and/or suppress proliferation and/or growth of cancerous cells. For simplicity, reference will be made generally to mPA7 or antibodies with the understanding that these methods apply to any of the CD46 binding embodiments described herein. These, conjugation generally refers to linking these components as described herein. The linking (which is generally fixing these components in proximate association at least for administration) can be achieved in any number of ways, as described below.

A radioactive molecule of this invention includes any radioisotope which is effective in destroying a cancerous cell. Examples include, but not limited to, cobalt-60 and X-rays. Additionally, naturally occurring radioactive elements such as uranium, radium, and thorium which typically represent mixtures of radioisotopes, are suitable examples of a radioactive molecule.

A toxin of the invention include, but not limited to, Taxol®, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. The antibodies of the invention can be internalized within the carcinoma cells to which they bind and are therefore particularly useful for therapeutic applications, for example, delivering into the cells toxins that need to be internalized for their adverse activity. Examples of such toxins include, but not limited to, saporin, calicheamicin, auristatin, and maytansinoid.

The antibodies or polypeptides of the invention can be conjugated (linked) to a radioactive molecule, a toxin, or other therapeutic agents, or to liposomes or other vesicles containing therapeutic agents covalently or non-covalently, directly or indirectly. The antibody may be linked to the radioactive molecule, the toxin, or the therapeutic molecule at any location along the antibody so long as the antibody is able to bind its target CD46.

A toxin or a therapeutic agent may be coupled (e.g., covalently bonded) to a suitable monoclonal antibody either directly or indirectly (e.g., via a linker group, or, alternatively, via a linking molecule with appropriate attachment sites, such as a platform molecule as described in U.S. Pat. No. 5,552,391). The toxin and therapeutic agent of the present invention can be coupled directly to the particular targeting proteins using methods known in the art. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

The antibodies or polypeptides can also be linked to a therapeutic agent via a microcarrier. Microcarrier refers to a biodegradable or a non-biodegradable particle which is insoluble in water and which has a size of less than about 150, 120 or 100 μm in size, more commonly less than about 50-60 μm, preferably less than about 10, 5, 2.5, 2 or 1.5 μm. Microcarriers include "nanocarriers", which are microcarriers have a size of less than about 1 μm, preferably less than about 500 nm. Such particles are known in the art. Solid phase microcarriers may be particles formed from biocompatible naturally occurring polymers, synthetic polymers or synthetic copolymers, which may include or exclude microcarriers formed from agarose or cross-linked agarose, as well as other biodegradable materials known in the art. Biodegradable solid phase microcarriers may be formed from polymers which are degradable (e.g., poly(lactic acid), poly(glycolic acid) and copolymers thereof) or erodible (e.g., poly(ortho esters such as 3,9-diethylidene-2,4,8,10-tetraoxaspiro[5.5] undecane (DETOSU) or poly(anhydrides), such as poly(anhydrides) of sebacic acid) under mammalian physiological conditions. Microcarriers may also be liquid phase (e.g., oil or lipid based), such liposomes, iscoms (immune-stimulating complexes, which are stable complexes of cholesterol, and phospholipid, adjuvant-active saponin) without antigen, or droplets or micelles found in oil-in-water or water-in-oil emulsions, provided the liquid phase microcarriers are biodegradable. Biodegradable liquid phase microcarriers typically incorporate a biodegradable oil, a number of which are known in the art, including squalene and vegetable oils. Microcarriers are typically spherical in shape, but microcarriers which deviate from spherical shape are also acceptable (e.g., elipsoid, rod-shaped, etc.). Due to their insoluble nature (with respect to water), microcarriers are filterable from water and water-based (aqueous) solutions.

The antibody or polypeptide conjugates of the present invention may include a bifunctional linker which contains both a group capable of coupling to a toxic agent or therapeutic agent and a group capable of coupling to the antibody. A linker can function as a spacer to distance an antibody from an agent in order to avoid interference with binding capabilities. A linker can be cleavable or non-cleavable. A linker can also serve to increase the chemical reactivity of a substituent on an agent or an antibody, and thus increase the coupling efficiency. An increase in chemical reactivity may also facilitate the use of agents, or functional groups on agents, which otherwise would not be possible. The bifunctional linker can be coupled to the antibody by means which are known in the art. For example, a linker containing an active ester moiety, such as an N-hydroxysuccinimide ester, can be used for coupling to lysine residues in the antibody via an amide linkage. In another example, a linker containing a nucleophilic amine or hydrazine residue can be coupled to aldehyde groups produced by glycolytic oxidation of antibody carbohydrate residues. In addition to these direct methods of coupling, the linker can be indirectly coupled to the antibody by means of an intermediate carrier such as an aminodextran. In these embodiments the modified linkage is via either lysine, carbohydrate, or an intermediate carrier. In one embodiment, the linker is coupled site-selectively to free thiol residues in the protein. Moieties which are suitable for selective coupling to thiol groups on proteins are well known in the art. Examples include disulfide compounds, α-halocarbonyl and α-halocarboxyl compounds, and maleimides. When a nucleophilic amine function is present in the same molecule as an α-halo carbonyl or carboxyl group the potential exists for cyclization to occur via intramolecular alkylation of the amine. Methods to prevent this problem are well known to one of ordinary skill in the art, for example by preparation of molecules in which the amine and α-halo functions are separated by inflexible groups, such as aryl groups or trans-alkenes, that make the undesired cyclization stereochemically disfavored. See, for example, U.S. Pat. No. 6,441,163 for preparation of conjugates of maytansinoids and antibody via a disulfide moiety.

One of the cleavable linkers that can be used for the preparation of antibody-drug conjugates is an acid-labile linker based on cis-aconitic acid that takes advantage of the acidic environment of different intracellular compartments such as the endosomes encountered during receptor mediated endocytosis and the lysosomes. See, for example, Shen et al., *Biochem. Biophys. Res. Commun.* 102:1048-1054 (1981) for the preparation of conjugates of daunorubicin with macromolecular carriers; Yang et al., *J. Natl. Canc. Inst.* 80:1154-1159 (1988) for the preparation of conjugates of daunorubicin to an anti-melanoma antibody; Dillman et al., *Cancer Res.* 48:6097-6102 (1988) for using an acid-labile linker in a similar fashion to prepare conjugates of daunorubicin with an anti-T cell antibody; Trouet et al., *Proc. Natl. Acad. Sci.* 79:626-629 (1982) for linking daunorubicin to an antibody via a peptide spacer arm.

An antibody (or polypeptide) of this invention may be conjugated (linked) to a radioactive molecule by any method known to the art. For a discussion of methods for radiolabeling antibody see "Cancer Therapy with Monoclonal AntibodiesT", D. M. Goldenberg ed. (CRC Press, Boca Raton, 1995).

An antibody (or polypeptide) of this invention may be linked to a labeling agent (alternatively termed "label") such as a fluorescent molecule, a radioactive molecule or any others labels known in the art. Labels are known in the art which generally provide (either directly or indirectly) a signal.

The ability of the antibodies, polypeptides and proteins of this invention, such as ability to inhibit growth of cancerous cells expressing CD46, ability to delay development of metastasis in an individual with cancer expressing CD46, ability to deliver a therapeutic agent, such as a toxin, or a radioactive compound, to cancerous cells expressing CD46, including ability to deliver a therapeutic agent into cancerous cells expressing CD46, may be tested using methods known in the art, some of which are described in the Examples.

The invention also provides compositions (including pharmaceutical compositions) comprising antibody mPA7 or mPA7 equivalent antibodies (which, as this disclosure makes clear, include all of the antibodies described herein) or polypeptides and a therapeutic agent.

Methods for Screening Monoclonal Antibodies

Several methods may be used to screen monoclonal antibodies that bind to Ag-PA7 (CD46). One method which may be employed is immunohistochemistry (IHC). Standard immunohistochemical techniques are known to those of average skill in the art. See, for example, *Animal Cell Culture Methods* (J. P. Mather and D. Barnes, eds., Academic Press, Vol. 57, Ch. 18 and 19, pp. 314-350, 1998). Biological samples (e.g., tissues) may be obtained from biopsies, autopsies, or necropsies. To ascertain if Ag-PA7 (CD46) is present only on cancerous cells, mPA7 may be used to detect the presence of Ag-PA7 (CD46) on tissues from individuals with cancer while other non-cancerous tissues from the individual suffering from cancer or tissues from individuals without cancer are used as a control. The tissue can be embedded in a solid or semi-solid substance which prevents damage during freezing (e.g., agarose gel or OCT) and then sectioned for staining. Cancers from different organs and at different grades can be used to screen monoclonal antibodies. Examples of tissues which may be used for screening purposes include but are not limited to ovary, breast, lung, prostate, colon, kidney, skin, thyroid, brain, heart; liver, stomach, nerve, blood vessels, bone, upper digestive tract, and pancreas. Examples of different cancer types which may be used for screening purposes include but are not limited to carcinomas, adenocarcinomas, sarcomas, adenosarcomas, lymphomas, and leukemias.

In yet another alternative, cancerous cells lines such as SK-Ov-3 (ATCC #HTB 77), LnCap (ATCC #CRL-1740), COLO 205 (ATCC #CCL 222), A549 (ATCC #CCL 185), PANC-1 (ATCC #CRL 1469), SK-BR-3 (ATCC #HTB 30), SK-MES-1 (ATCC #HTB 58), HT-29 (HTB-38), SW 480 (ATCC #CCL 228), AsPC-1 (ATCC #CRL 1682), Capan-1 (ATCC #HTB 79), CFPAC-1 (ATCC #CRL 1918), HPAF-II (ATCC #CRL-1997), HS-700T (ATCC #HTB 147), Du-145 (ATCC #HTB-81), CaLu-1 (ATCC #HTB-54), 786-O (ATCC #CRL-1932). CaKi-2 (ATCC #HTB-47), A498 (ATCC #HTB-44), BT474 (ATCC #HTB-20), and PC-3 (ATCC #CRL 1435) and normal cells from their respective tissues may be used to screen for monoclonal antibodies which are specific for cancerous tissue. Primary, or low passage, cell cultures derived from normal tissues from different organs, including but not limited to, ovary, breast, lung, prostate, colon, kidney, skin, thyroid, aortic smooth muscle, and endothelial cells can be used as negative controls. The cancerous or non-cancerous cells can be grown on glass slides or coverslips, or on plastic surfaces, or prepared in a CellArray™, as described in WO 01/43869, and screened for the binding of antibody using IHC as described above for tissues. Alternatively, cells may be removed from the growth surface using non-proteolytic means and spun into a pellet which is then embedded and treated as tissues for IHC analysis as described above. In another alternative, single cells may be screened by incubating with the primary antibody, a secondary "reporter" antibody linked to a fluorescent molecule and then analyzed using a fluorescent activated cell sorting (FACS) machine.

Several different detection systems may be utilized to detect binding of antibodies to tissue section. Typically, immunohistochemistry involves the binding of a primary antibody to the tissue and then a secondary antibody reactive against the species from the primary antibody was generated and conjugated to a detectable marker (e.g., horseradish peroxidase, HRP, or diaminobenzedine, DAB). One alternative method that may be used is polyclonal mirror image complementary antibodies or polyMICA®. polyMICA® (polyclonal Mirror Image Complementary Antibodies) technique, described by D. C. Mangham and P. G. Isaacson (Histopathology (1999) 35(2):129-33), can be used to test binding of primary antibodies (e.g., mPA7) to normal and cancerous tissue. Several kinds of polyMICA®. Detection kits are commercially available from The Binding Site Limited (P.O. Box 4073 Birmingham B29 6AT England). Product No. HK004.D is a polyMICA® Detection kit which uses DAB chromagen. Product No. HK004.A is a polyMICA® Detection kit which uses AEC chromagen. Alternatively, the primary antibody may be directly labeled with the detectable marker.

The first step in IHC screening to select for an appropriate antibody is the binding of primary antibodies raised in mice (e.g., mPA7) to one or more immunogens (e.g., cells or tissue samples). In one embodiment, the tissue sample is sections of frozen tissue from different organs. The cells or tissue samples can be either cancerous or non-cancerous.

Frozen tissues can be prepared, sectioned, with or without fixation, and IHC performed by any of a number of methods known to one familiar with the art. See, for example, Stephan et al. *Dev. Biol.* 212: 264-277 (1999), and Stephan et al. *Endocrinology* 140: 5841-54 (1999).

Monoclonal antibodies that are cross-reactive with human cells and that bind to cancerous cells or tissues, but not to normal cells or tissues to the same degree, are selected. Monoclonal antibodies that bind to antigens expressed on one or more cancer types but not to normal cells are also selected. mPA7 is an example of an antibody that binds to an antigen present on a number of different cancers, but has limited binding to normal tissues. In accordance with the Budapest Treaty, the hybridoma which produces mPA7 has been deposited in the American Type Culture Collection (ATCC) 10801 University Blvd., Manassas Va. 20110-2209 on Sep. 18, 2001 with a Patent Deposit Designation of PTA-3706.

Epitope mapping may be used to further characterize the antibody. Commercially available services (e.g., Pepscan Systems, P.O. Box 2098, 8203 AB Lelystad, The Netherlands) may be used to determine the epitope(s) on the antigen to which an antibody, such as mPA7, binds.

Methods of Identifying and Characterizing Ag-PA 7, CD46

Several methods may be employed to identify the antigen for mPA7, some of which are described in the Examples. One method is to utilize antibodies for affinity purification. Cell lysates/extracts or tissue homogenates/extracts may be applied to an affinity resin in which the antibody mPA7 has been attached to a solid support. The samples to be extracted can be obtained from any number of sources, including but not limited to normal or cancerous tissues, biological samples from individuals with a cancer or another disease state, commercial sources (e.g., American Type Culture Collection or ATCC, Manassas, Va.), or a cell line. The antibodies that are used for affinity purification may be obtained in various manners which are discussed in detail below. Once the antigen has been bound to the support, the antigen can be eluted using different reagents. These reagents include but are not limited to low pH reagents and chemical denaturants (e.g., urea or guanidine HCl). See, for example, *Current Protocols in Immunology* (J. E. Coligan et al., eds., Volume 2, 1991, 8.2.1-8.2.9). This method is further detailed in Example 5.

The purified antigen may be used for sequencing using standard sequencing methods known in the art (e.g., Edman degradation). If peptide sequences are obtained, then degenerate primers or probes can be made from the peptide sequences. The probes can then be hybridized to cDNA libraries in order to identify those bacteria containing inserts that contain the DNA encoding the protein under study. See, for example, Sambrook et al. or Ausubel et al. above. The antigen of the antibody mPA7 was determined to be CD46 (membrane cofactor protein, MCP). The sequence of CD46 is disclosed in U.S. Pat. Nos. 5,514,787, 5,846,715, 5,552,381, 5,703,046, 6,218,520.

Another method which was used for identifying and characterizing to which mPA7 binds is to use Western blotting techniques. Ag-PA7 was identified in one aspect by Western blotting with cell lysates from various human cancers and monoclonal antibody mPA7, the hybridoma producing this antibody was deposited at the American Type Culture Collection (ATCC) 10801 University Blvd., Manassas Va. 20110-2209 on Sep. 18, 2001 with a Patent Deposit Designation of PTA-3706. As is known to one of skill in the art, Western blotting can involve running cell lysates and/or cell fractions on a denaturing or non-denaturing gel, transferring the proteins to nitrocellulose paper, and then probing the blot with an antibody (e.g., mPA7) to see which proteins are bound by the antibody. This procedure is detailed further in Example 4. The antigen was purified for further characterization as described in Example 5.

Another method that can be used to characterize antigens to which mPA7 bind is mass spectrometry analysis. Several types of mass spectrometry analysis may be performed. In one approach, the masses of a tryptic digest of the protein were measured by matrix assisted laser desorption/ionization (MALDI) time-of-flight mass spectrometry (MALDI-TOF-MS) and the resulting list of peptide masses are used as a "fingerprint" of the protein in sequence database searches. In matrix assisted laser desorption/ionization (MALDI), the peptides are co-crystallized with a large excess of a light absorbing matrix. Irradiation of the crystals by a pulsed laser beam results in the rapid sublimation of matrix and the embedded peptide molecules and the generation of intact gas phase ions. For peptides, protonated, singly charged molecular ions are usually formed. The mass/charge ratio (m/z) is measured at high mass accuracy time-of-flight analysis, optionally employing delayed-extraction and/or a reflectron. The retrieved sequences are evaluated by mass analysis of the peptides, matching the peptide masses in the MALDI spectrum after accounting for common modifications such as oxidation, acrylamidation of cysteine and missed cleavages and the use of secondary information (apparent isoelectric point and/or molecular weight). If any ambiguity about the identification by MALDI-TOF-MS still exists, the results can be verified by mass spectrometric peptide sequencing. These and other procedures for using mass spectroscopy to identify known proteins are reviewed in *Use of Mass Spectrometry to Study Signaling Pathways* (A. Pandey, J. S. Andersen, and M. Mann; 2000).

The surface antigen recognized by a monoclonal antibody of the present invention is first isolated by any method described above and alternatively, can be isolated by any methods known to the average skilled artisan. The protein band which was bound by the antibody mPA7 was characterized by first digesting the purified protein with a protease, which results in a mixture of peptides. The peptides were then analyzed by MALDI mass spectroscopy and the mass spectrometry pattern was compared to patterns of other proteins. In this manner, the antigen for mPA7, Ag-PA7, was determined to be CD46 as further described in Example 6.

Another mass spectroscopy method which may be used is nanoelectrospray tandem mass spectrometry. In this method, a solution of peptide molecules is passed through a needle maintained at a high potential. At the end of the needle, the solution is dispersed into a fine mist of small, highly charged droplets containing peptide molecules. These small droplets evaporate rapidly resulting in the release of multiple charged molecular ions into the gas phase. Once the peptides are in the gas phase, they are transported through an orifice into a mass spectrometer where they are separated and detected according to their mass to charge (m/z) ratio. Nanoelectrospray refers to a refined version of electrospray where an extremely fine needle disperse the sample at flow rates in the nanoliter per minute range. This greatly reduces the droplet diameter and enhances the sensitivity of detection of peptides. Electrospray tends to be more sensitive to the presence of salts than MALDI-TOF-MS. Therefore, the samples are first desalted by methods known to skilled artisans. The electrospray ion source is compatible with mass spectrometers that allow peptide sequencing (the most common are triple quadrupole, ion trap, or quadrupole-time-of-flight mass spectrometers). In low-level protein identifications, the peptide signals are often obscured by the chemical background or signals from contaminants. High-resolution instruments (e.g., a quadrupole-time-of-flight instrument) help to resolve peptides from the chemical background. Alternatively, in a triple quadrupole instrument, a precursor-ion scan enables selective detection of peptides in the presence of nonpeptide contaminants.

Ag-PA7 can be further characterized by its location within a cell. Without being bound by theory, Ag-PA7 (CD46) is a cell-associated antigen that is expressed at least on the surface of a cell. Since the method of generating monoclonal antibody mPA7 involved using intact cells as immunogen, the monoclonal antibody that was generated was most likely against an antigenic determinant on the surface of the cell. Such cell surface proteins may, however, also be present inside the cell, or secreted or released from the cell surface, in addition to being present on the cell surface. Whether the antigen is present on the cell surface or interior or released from the cell may differ depending on the type of cells, or alternatively may depend on the different stages of the cell cycle, different developmental stages, or in diseased compared to non-diseased (i.e., normal), cells.

Further characterization of antigen can be accomplished by determining expression patterns on different tissues or cells, copy number on cells and/or tissues, and by the antibodies which bind to it. In one aspect, the expression patterns was determined by using immunohistochemical techniques with biological samples. The expression pattern of the antigen can be assessed in individuals with and without cancer or alternatively another disease state. Copy number of antigens can be determined by using standard Scatchard analysis. Determining expression patterns of Ag-PA7 was described in further detail in Examples 8-11.

Methods of Using Ag-PA 7, CD46

Once an antigen (e.g., Ag-PA7) has been identified and characterized, the information about the antigen (e.g., sequence) may be used for various purposes. The antigen for antibody mPA7 was determined to be CD46. The sequence of CD46 has been disclosed in U.S. Pat. Nos. 5,846,715, 5,514,787, 5,552,381, 5,703,046, and 6,218,520. In one aspect, the sequence of Ag-PA7 (CD46) may be used to make antibodies that bind to it. For example, Ag-PA7 (CD46) sequence can be cloned into an expression vector and expressed in a suitable host cell to make an immunogen for animal injections and subsequent generation of hybridomas. Methods of making antibodies are described below. In another aspect, antibody mPA7 sequence may be used to make an antibody recombinantly. Methods of making recombinant antibodies are well-known in the art. See, for example, *Current Protocols in Immunology* (J. E. Coligan et al., eds., 1991) and U.S. Pat. Nos. 5,665,570; 5,677,425; 5,760,185; 5,773,247; and 5,929,212. In yet another aspect, Ag-PA7 (CD46) can be used to make antibodies as described herein and the antibodies which bind to Ag-PA7 may be used for epitope mapping and/or cross competition with other antibodies for discovery of new and potential biologically functional epitopes.

Another use for Ag-PA7 (CD46) is for drug screening purposes as a possible receptor for a protein, a peptide, or a small molecule ligand. Drugs, compounds, proteins, small molecules, and pharmaceutical compositions can be tested for their ability to bind to Ag-PA7 alone or in combination with antibody mPA7 and any other CD46 binding moieties described herein and any effects or enhanced effects resulting from such binding. Ag-PA7 may be bound to a substrate and monitored for effects. Such effects may include but are not limited to changes in intracellular pathway regulation, apoptosis, cellular activation, cellular metabolism, or cellular anergy. Binding of Ag-PA7 may elucidate its biological role (e.g., regulatory protein, protein associated with growth, differentiation, or development, etc.).

Another use for Ag-PA7 (CD46) is for purification of antibodies against Ag-PA7. In one embodiment, mammals may be immunized with any immunogen, (e.g., cancerous cells) and their splenocytes can be removed and used to make hybridomas. The hybridoma supernatants may be passed over an affinity column in which Ag-PA7 is immobilized.

Ag-PA7 (CD46) as a protein or as nucleic acid may be used for vaccination purposes (e.g., active immunization). In some cases, Ag-PA7 can be administered for vaccination with an adjuvant. In other cases, an adjuvant is not used and Ag-PA7 is administered neat. While the routes of administration are varied for vaccinations, standard routes of vaccination are injection and oral ingestion. See, for example, U.S. Pat. Nos. 6,221,644; 6,117,653; 6,110,724; and 5,932,225.

Yet another use for Ag-PA7 (CD46) is to use Ag-PA7 or portions thereof for high-throughput screening. For example, Ag-PA7 DNA sequences may be immobilized to solid or semi-solid substrate and DNA isolated from biological samples from a panel of individuals can be used to determine if hybridization occurs. In one embodiment, complimentary strands of nucleic acids are used to optimize hybridization. This approach can be useful for screening individuals for cancerous, or other, cells which express Ag-PA7.

Methods of Diagnosing Cancer Using mPA7, mPA7 Equivalent Antibodies or Polypeptides which Bind to CD46

Monoclonal antibody mPA7 and equivalent antibodies or polypeptides derivatives of mPA7 which bind CD46 made by the methods disclosed herein may be used to identify or detect the presence or absence of cancerous cells in a variety of tissues, including but not limited to, ovary, breast, lung, prostate, colon, kidney, skin, thyroid, brain, heart, liver, stomach, nerve, blood vessels, bone, upper digestive tract, and pancreas for purposes of diagnosis. For simplicity, reference will be made generally to mPA7 or antibodies with the understanding that these methods apply to any of the CD46 binding embodiments described herein. Detection generally involves contacting cells with an antibody or a polypeptide described herein that binds to CD46 and the formation of a complex between Ag-PA7 (CD46) and an antibody (e.g., mPA7, a humanized antibody of mPA7, a human antibody or any other CD46 binding moiety) which binds specifically to Ag-PA7 (CD46). The formation of such a complex can be in vitro or in vivo. Without being bound by theory, monoclonal antibody mPA7 can bind to Ag-PA7 (CD46) through the extracellular domain of Ag-PA7 (CD46).

In some embodiments, methods are provided for detecting presence or absence of prostate cancerous cells by detecting CD46 from cells. CD46 from prostate cancerous cells can be detected using any method, including but not limited to detection of CD46 mRNA, and detection of CD46 protein. Any CD46 binding moiety can be used, such as those described herein (e.g., mPA7, mPA7 equivalent antibodies such as those which bind the same epitope as mPA7). As used herein, detection may include qualitative and/or quantitative detection and may include comparing the level measured to a normal prostate cell for an increased level of expression of CD46 in cancerous cells.

One method of using the antibodies for diagnosis is in vivo tumor imaging by linking the antibody to a labeling moiety (e.g., a fluorescent agent, a radioactive or radioopaque agent), administering the antibody to the patient and using an x-ray or other imaging machine to visualize the localization of the labeled antibody at the surface of cancer cells expressing the antigen. Labeling moieties are known in the art.

In other methods, the cancerous cells are removed and the tissue prepared for immunohistochemistry by methods well known in the art (e.g., embedding in a freezing compound, freezing and sectioning, with or without fixation; fixation and paraffin embedding with or without various methods of antigen retrieval and counterstaining). The monoclonal antibodies may also be used to identify neoplasms at different stages of development. The antibodies may also be used to determine which patients' tumors express the antigen on their surface at a pre-determined level and are thus candidates for immunotherapy using antibodies directed against said antigen.

Antibodies (or polypeptides) recognizing the antigen may also be used to create diagnostic immunoassays for detecting antigen released or secreted from living or dying cancer cells in bodily fluids, including but not limited to, blood, saliva, urine, pulmonary fluid, or ascites fluid. As discussed in further detail in the Examples, mPA7 can bind to various forms cancer in different stages from tissues including but not limited to ovary, breast, lung, prostate, colon, kidney, and pancreas. Methods of using mPA7 for diagnostic purposes is useful both before and after any form of anti-cancer treatment, e.g., chemotherapy or radiation therapy, to determine which tumors are most likely to respond to a given treatment, patient prognosis, tumor subtype or origin of metastatic disease, and progression of the disease or response to treatment.

Methods of Using mPA 7, mPA 7 Equivalent Antibodies or Polypeptides for Therapeutic Purposes Monoclonal antibody mPA7 and equivalent antibodies (as well as other polypeptides embodiments of the invention) made by the methods disclosed herein may be used for therapeutic purposes in individuals with cancer, including but not limited to cancer of the ovary, breast, lung, prostate, colon, kidney, or pancreas. In some embodiments, the cancer is prostate (provided that the prostate cancer cells bind to the antibody or polypeptide). These therapeutic methods also apply to the linked embodiments described above. For simplicity, reference will be made generally to mPA7 or antibodies with the understanding that these methods apply to any of the CD46 binding embodiments described herein, including but not limited to humanized antibodies and human antibodies described herein including linked embodiments. Therapy with mPA7 can involve formation of complexes of mPA7 and Ag-PA7 (CD46) both in vitro and/or in vivo as described above. In one embodiment, monoclonal antibody mPA7 can bind to and reduce the growth and/or proliferation of cancerous cells (e.g., prostate cancer cells). In another embodiment, monoclonal antibody mPA7 can bind to and induce apoptotic cell death in the cancer cell. In another embodiment, monoclonal antibody mPA7 can bind to cancerous cells and delay the development of metastasis. In another embodiment, monoclonal antibody mPA7 can bind to cancerous cells and deliver a therapeutic agent (such as a toxin, or a radioactive compound) linked to mPA7 to cancerous cells. For some embodiments, therapeutic agent (such as a toxin) is introduced into a cell (i.e., is internalized). Particularly suitable agents for these methods include agents which are active inside the cell. Examples of such agents include but not limited to saporin, calicheamicin, auristatin, and maytansinoid. In some embodiments, these agents are linked to mPA7 and are internalized in prostate, ovarian, breast, or colon cancer cells. Generally, in these embodiments an effective amount (an amount sufficient to deliver a therapeutic agent to and/or into target cancerous cells) is administered to an individual. In yet another embodiment, an individual with cancer is given palliative treatment with mPA7. Palliative treatment of a cancer patient involves treating or lessening the adverse symptoms of the disease, or iatrogenic symptoms resulting from other treatments given for the disease without directly affecting the cancer progression. This includes treatments for easing of pain, nutritional support, sexual problems, psychological distress, depression, fatigue, psychiatric disorders, nausea, vomiting, etc.

This invention also provides methods of inhibiting growth and/or proliferation of prostate, lung, breast, ovarian, pancreatic, renal cancer cells using an antibody or other embodiments that bind to CD46. Antibodies that bind to CD46 have been described. See, for example, PCT WO 02/18948; Sparrow et al. *Hum. Immunol.* 7:1 (1983); Seya et al. *J. Exp. Med.* 163:837 (1986); His et al. *Am. J. Reprod. Immunol. Microbiol.* 18:21 (1988). The method of testing activity of an antibody in inhibiting growth and/or proliferation of cancer cells are known in the art and are described in detail in Examples 12 and 13.

This invention also provides methods of inhibiting growth and/or proliferation of cancer cells (such as prostate, lung, breast, colon, ovarian, pancreatic, renal cancer cells) using mPA7 antibody or an antibody which perferentially binds to the same epitope as mPA7 preferentially binds.

This invention also provides methods of inhibiting growth and/or proliferation of vescular endothelial cells expressing CD46 (such as venous endothelial cells) using mPA7 or mPA7 equivalent antibodies or polypeptides described herein. See Example 14. This invention also provides methods of inhibiting angiogenesis using mPA7 or mPA7 equivalent antibodies or polypeptides described herein. In some embodiments of these methods (inhibiting growth and/or proliferation and/or angiogenesis) the antibody is linked to a therapeutic agent. The therapeutic agent may be any therapeutic agent described herein, including but not limited to saporin, calicheamicin, auristatin, or maytansinoid.

In yet another embodiment, mPA7 or any of the CD46 embodiments described herein can bind to CD46 expressing cancerous cells and induces an active immune response against the cancerous cells expressing Ag-PA7 (CD46). In some cases, the active immune response can cause the death of the cancerous cells (e.g., mPA7 binding to cancer cells inducing apoptotic cell death), or inhibit the growth (e.g., block cells cycle progression) of the cancerous cells. In other cases, mPA7 or any of the CD46 antibodies described herein can bind to cancerous cells and antibody dependent cellular cytotoxicity (ADCC) can eliminate cancerous cells to which mPA7 binds. Accordingly, the invention provides methods of stimulating an immune response comprising administering any of the compositions described herein.

In some cases, mPA7 binding can also activate both cellular and humoral immune responses and recruit more natural killer cells or increased production of cytokines (e.g., IL-2, IFN-γ, IL-12, TNF-α, TNF-β, etc.) that further activate an individual's immune system to destroy cancerous cells. In yet another embodiment, mPA7 can bind to cancerous cells, and macrophages or other phagocytic cell can opsonize the cancerous cells.

In some embodiments, the invention provides methods of conferring passive immunity comprising administering any of the compositions described herein.

The invention provides methods of delivering any of the compositions (including conjugates) described herein to a CD46 expressing cell, such as a CD46 expression cancer cells. These methods entail administering the compositions (including conjugates) described herein to an individual. In some embodiments, the methods provide for introducing, for example, a conjugate into a target cell. In yet another embodiment, mPA7 can be conjugated to a therapeutic agent (such as a radioactive molecule, a toxin, e.g., saporin, calicheamicin, auristatin, or maytansinoid, or other chemotherapeutic molecule) or to liposomes or other vesicles containing chemotherapeutic compounds and administered to an individual to target these compounds to the cancer cell containing the antigen recognized by the antibody and thus eliminate cancerous cells. In yet another embodiment, the antibody can be employed as adjuvant therapy at the time of the surgical removal of a cancer expressing the antigen in order to delay the development of metastasis. The antibody can also be administered before surgery (neoadjuvant therapy) in a patient with a tumor expressing the antigen in order to decrease the size of the tumor and thus enable or simplify surgery, spare tissue during surgery, and/or decrease the resulting disfigurement.

Various formulations of mPA7 and equivalent antibodies or fragments (e.g., Fab, Fab', F(ab')$_2$, Fv, Fc, etc.), such as chimeric antibodies, single chain (ScFv), mutants thereof, fusion proteins comprising an antibody portion, humanized antibodies, and any other modified configuration of mPA7 that comprises an antigen Ag-PA7 (CD46) recognition site of the required specificity, may be used for administration. In some embodiments, mPA7 antibodies or various formulations of mPA7 thereof may be administered neat. In other embodiments, mPA7 or various formulations of mPA7 (including any composition embodiment described herein) thereof and a pharmaceutically acceptable excipient are administered, and may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in *Remington, The Science and Practice of Pharmacy* 20th Ed. Mack Publishing (2000).

Generally, these agents are formulated for administration by injection (e.g., intraperitoneally, intravenously, subcutaneously, intramuscularly, etc.), although other forms of administration (e.g., oral, mucosal, etc) can be also used. Accordingly, mPA7 antibody and equivalents thereof are preferably combined with pharmaceutically acceptable vehicles such as saline, Ringer's solution, dextrose solution, and the like. The particular dosage regimen, i.e., dose, timing and repetition, will depend on the particular individual and that individual's medical history. Generally, any of the following doses may be used: a dose of at least about 50 mg/kg body weight; at least about 10 mg/kg body weight; at least about 3 mg/kg body weight; at least about 1 mg/kg body weight; at least about 750 µg/kg body weight; at least about 500 µg/kg body weight; at least about 250 ug/kg body weight; at least about 100 µg/kg body weight; at least about 50 µg/kg body weight; at least about 10 ug/kg body weight; at least about 1 µg/kg body weight, or more, is administered. Empirical considerations, such as the half-life, generally will contribute to determination of the dosage. Antibodies which are compatible with the human immune system, such as humanized antibodies or fully human antibodies, may be used to prolong half-life of the antibody and to prevent the antibody being attacked by the host's immune system.

In some individuals, more than one dose may be required. Frequency of administration may be determined and adjusted over the course of therapy, and is based on reducing the number of cancerous cells, maintaining the reduction of cancerous cells, reducing the growth and/or proliferation of cancerous cells, or delaying the development of metastasis. The presence of cancerous cells can be identified by any number of methods known to one of skill in the art or discussed herein (e.g., detection by immunohistochemistry or flow cytometry of biopsies or biological samples). In some cases, sustained continuous release formulations of mPA7 antibodies may be appropriate. Various formulations and devices for achieving sustained release are known in the art.

In one embodiment, dosages for mPA7 antibodies may be determined empirically in individuals who have been given one or more administration(s). Individuals are given incremental dosages of mPA7. To assess efficacy of mPA7 or other equivalent antibody, markers of the specific cancer disease state can be monitored. These markers include: direct measurements of tumor size via palpation or visual observation; indirect measurement of tumor size by x-ray or other imaging techniques; an improvement as assessed by direct tumor biopsy and microscopic examination of the tumor sample; the measurement of an indirect tumor marker (e.g., PSA for prostate cancer), a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of cancer, the stage of cancer, whether the cancer has begun to metastasize to other location in the individual, and the past and concurrent treatments being used.

Other formulations include suitable delivery forms known in the art including, but not limited to, carriers such as liposomes. See, for example, Mahato et al. (1997) *Pharm. Res.* 14:853-859. Liposomal preparations include, but are not limited to, cytofectins, multilamellar vesicles and unilamellar vesicles.

In some embodiments, more than one antibody may be present. The antibodies can be monoclonal or polyclonal. Such compositions may contain at least one, at least two, at least three, at least four, at least five different antibodies that are reactive against carcinomas, adenocarcinomas, sarcomas, or adenosarcomas. mPA7 antibody can be admixed with one or more antibodies reactive against carcinomas, adenocarcinomas, sarcomas, or adenosarcomas in organs including but not limited to ovary, breast, lung, prostate, colon, kidney, skin, thyroid, bone, upper digestive tract, and pancreas. A mixture of antibodies, as they are often denoted in the art, may be particularly useful in treating a broader range of population of individuals.

Assessment of disease is performed using standard methods in the arts, such as imaging methods and monitoring appropriate marker(s).

Kits Comprising Antibodies and Polypeptides of the Invention which Bind to Ag-PA 7 (CD46)

The invention also provides kits comprising antibodies or any of the compositions described herein which bind to CD46 for use in diagnosis and/or therapy. Accordingly, the kits comprise an antibody which can bind to CD46 preferentially and/or form a complex with CD46 (useful, for example, for detecting breast, colon, lung, ovarian, pancreatic, prostate, or renal cancerous cells). In some embodiments, the kits comprise antibody mPA7 or an antibody that preferentially binds to the same epitope as mPA7 preferentially binds. In some embodiments, the kits comprise antibody mPA7 or an antibody that preferentially binds to the same epitope as mPA7 preferentially binds linked to a therapeutic agent or a labeling agent. These kits may further include instruction and/or reagents for linking the antibody or any antibody or polypeptide embodiments described herein to the therapeutic agent(s) or the labeling agent(s). In some aspects, the binding of an antibody (e.g., monoclonal, polyclonal, human, humanized, etc.) to CD46 is used for diagnosing cancer in an individual, for example, kits for detecting presence or absence of cancerous cells, and kits for detecting presence or absence of breast, colon, lung, ovarian, pancreatic, prostate, or renal cancerous cells. In other aspects, the kits may be used, for example, to treat an individual with cancer or a family history of cancer. Kits for treating individual with cancer include but not limited to kits for inhibiting growth and/or proliferation of cancer cells, such as prostate, for delivering a therapeutic agent to cancerous cells, for delivering a therapeutic agent into cancerous cells such as prostate, ovarian, breast, or colon cancer cells. The kits of this invention are in suitable packaging, and may optionally provide additional components such as, buffers and instructions for determining binding to Ag-PA7 (CD46), such as capture reagents, developing reagents, labels, reacting surfaces, means for detection, control samples, and interpretive information. The instructions may be for any measurement of antigen binding, including, but not limited to, those assays described herein. In other embodiments, the instructions may be for any of the methods described herein, including: instructions for inhibiting grow and/or proliferation of cancerous cells such as prostate, for delivering a therapeutic agent to cancerous cells, for delivering a therapeutic agent into cancerous cells such as prostate, ovarian, breast, or colon cancer cells. In some embodiments, reagents described above are supplied such that multiple measurements may be made, such as allowing for measurements in the same individual over time or multiple individuals. Any appropriate means for detecting binding of the antibodies may be employed (and provided in the kits) such as a labeled anti-human antibody, wherein the label may be an enzyme, fluorophore, chemiluminescent material radioisotope or coenzyme. Generally, the label used will be an enzyme.

The following examples are provided to illustrate, but not to limit, the invention.

EXAMPLES

Example 1

Preparation of Human Pancreatic Epithelial Progenitor (hPED) Cells as an Immunogen Fetal pancreases (gestational age 14-22 weeks) were mechanically pulled apart by microdissection under a stereo microscope prior to enzymatic dissociation. Enzyme treatment consisted of placing the partly dissociated tissue in 1 ml Ca-free and Mg-free PBS containing 1 mg/ml collagenase-4, 1 mg/ml soybean trypsin inhibitor, 1 mg/ml Hyaluronidase and 50 µg/ml DNAase for 15 minutes at 37 degrees Celsius.

Cell aggregates were layered on top of a 5% (by volume) BSA gradient and washed by centrifugation for 6 minutes at 1100 rpm. Pelleted cells which were still in aggregate form were resuspended in growth medium consisting of CMRL 1066 nutrient medium containing the following factors:

| | |
|---|---|
| Insulin | 10 µg/ml |
| Transferrin | 10 µg/ml |
| Epidermal growth factor | 5 ng/ml |
| Ethanolamine | $10^{-6}$ M |
| Phosphoethanolamine | $10^{-6}$ M |
| Selenium | $2.5 \times 10^{-8}$ M |
| Triiodothyronine | $10^{-12}$ M |
| Progesterone | $10^{-9}$ M |
| Hydrocortisone | $10^{-9}$ M |
| Forskolin | 1 µM |
| Heregulin | 10 nM |
| Aprotinin | 25 µg/ml |
| Bovine pituitary extract | 75 µg/ml protein |
| Gentamycin | 100 µg/ml |

Resuspended cell aggregates were aliquoted into fibronectin-coated wells (6-12) of a 24-well dish and incubated at 37 degrees Celsius in a humidified 5% $CO_2$ incubator for 72 hours. After 72 hours, the epithelial cell aggregates were transferred to fibronectin coated dishes in F12/DMEM plus the above factors. The aggregates attached and formed adherent monolayers. Both the aggregates and the adherent monolayers, up to passage 5, were used as immunogens to generate monoclonal antibodies.

Example 2

Generation of Monoclonal Antibodies Against hPED

A non-denaturing adjuvant (Ribi, R730, Corixa, Hamilton Mont.) was rehydrated to 4 ml in phosphate buffered saline. 100 µl of this rehydrated adjuvant was then diluted with 400 µl of Hank's Balanced Salt Solution and this was subsequently gently mixed with the cell pellet used for immunization. Approximately $10^6$ hPED cells per mouse were injected into Balb/c mice via foot-pad, once a week. After 6 weeks of weekly injection, a drop of blood were drawn from the tail of each immunized animal to test the titer of antibodies against hPED using FACS analysis. When the titer reached at least 1:2000, the mice were sacrificed in a $CO_2$ chamber followed by cervical dislocation. Lymph nodes were harvested for hybridoma preparation.

Lymphocytes from mice with the highest titer were fused with the mouse myeloma line X63-Ag8.653 using 35% polyethylene glycol 4000. On day 10 following the fusion, the hybridoma supernatants were screened for the presence of hPED-specific monoclonal antibodies by fluorescence activated cell sorting (FACS). Conditioned medium from each hybridoma was incubated for 30 minutes with a combined aliquot of PC3, Colo-205, LnCap, or Panc-1 cells. After incubation, the cell samples were washed, resuspended in 0.1 ml diluent and incubated with 1 µg/ml of FITC conjugated F(ab')2 fragment of goat anti-mouse IgG for 30 min at 4° C. The cells were washed, resuspended in 0.5 ml FACS diluent and analyzed using a FACScan cell analyzer (Becton Dickinson; San Jose, Calif.). Hybridoma clones were selected for further expansion, cloning, and characterization based on their binding to the surface of one or more of the cell lines as assessed by FACS. A hybridoma making a monoclonal antibody designated mPA7 which binds an antigen designated Ag-PA7 and an epitope on that antigen designated Ag-PA7.1 was selected.

Example 3

Screening a Panel of Antibodies Against the Antigen Source hPED cells were detached from tissue culture flasks in the presence of 0.5 mM EDTA, centrifuged at 1400 rpm for 5 minutes and resuspended in PBS containing 1% BSA and 2 mM EDTA (FACS diluent). The cells were counted and adjusted to $10^7$ cells/ml. About 0.1 ml of cells were incubated with 100 µl hybridoma supernatant or 1 µg of purified monoclonal antibodies in 100 µl FACS diluent for 30 mm at 37° C. Monoclonal antibodies were purified from tissue culture supernatant using protein-G affinity chromatography. The following materials were used for the antibody purification process: hybridoma tissue culture supernatant, Immunopure® (G) IgG binding buffer (Pierce #21011 Rockford, Ill.), Immunopure® IgG Elution Buffer (Pierce #21009), concentrated HCl (for adjusting pH), Corning 1 liter PES (polyether sulfone), 0.22 µm filter (Corning #431098, Corning, N.Y.), Amersham Pharmacia GradiFracTM™ System (Amersham Pharmacia, Piscataway, N.J.), Protein-G Sepharose® 4 Fast Flow (Amersham Pharmacia #17-0618-02), Stripping buffer which is 3M KSCN/50 mM Tris pH 7.8, and PBS (phosphate buffered saline) 3M Tris pH 9.0.

To purify the mPA7 antibody, the volume of supernatant was measured and an equal volume of binding buffer was added to the supernatant. The mixture was allowed to equilibrate to room temperature. The supernatant was clarified by passage through a 0.22 µm filter. The supernatant was loaded on to a protein-G column using the GradiFrac™ system (Pharmacia Biotech). The column was washed with 5-10 column volumes of binding buffer. The monoclonal antibodies were eluted with the elution buffer and 2 ml fractions were collected. An $OD_{280}$ reading of the fractions were obtained and the fractions containing monoclonal antibodies were pooled. The eluted monoclonal antibody fractions were neutralized by adding 1/20 volume of 3M Tris. The sample was dialyzed in 1×PBS at 40° C. (with 3 buffer changes of at least 3 hours per change). The purified monoclonal antibodies were sterile filtered (0.2 uM) and stored at 2-8° C.

After purification of the mPA7 monoclonal antibody from the hybridoma supernatant, it was re-tested for binding to hPED cells. The cell samples were prepared as described above in Example 6 and incubated with the purified antibody at various concentrations After incubation the cells were washed, resuspended in 0.1 ml diluent and incubated with 1 µg of FITC conjugated F(ab')2 fragment of goat anti-mouse IgG for 30 min at 4° C. The cells were washed, resuspended in 0.5 ml FACS diluent and analyzed using a FACScan cell sorter (Becton Dickinson; San Jose, Calif.). A shift to the right on the FACScan histogram indicated that the purified antibody still bound to the hPED cells.

Example 4

Identification and Characterization of Antigen Ag-PA7

A cell pellet of proximately 25 ul packed cell volume of the LnCap cell line (commercially available from ATCC) was lysed by first diluting the cells to 0.5 ml in water followed by freezing and thawing three times. The solution was centrifuged at 14,000 rpm. The resulting pellet, containing the cell membrane fragments, was resuspended in 50 ul of SDS sample buffer (Invitrogen, Carlsbad, Calif.). The sample was heated at 80° C. for 5 minutes and then centrifuged for 2 minutes at 14,000 rpm to remove any insoluble materials. Other cell lines that express Ag-PA7 and can be used for purification include HPAF, Colo-205 and Panc-1, or the other cell lines which bind mPA7 as indicated in Table 3.

The samples were analyzed by Western blot using a 4 to 20% Tris-Glycine SDS polyacrylamide gradient gel (Invitrogen; Carlsbad Calif.) following the manufacturers' directions. Ten microliters of membrane sample were applied to one lane on the polyacrylamide gel. A separate ten microliter sample was reduced first by the addition of 2 µL of dithiothreitol (100 mM) with heating at 80° C. for 2 minutes and then loaded into another lane. The pre-stained molecular weight markers SeeBlue® Plus2 (Invitrogen; Carlsbad, Calif.) were used to assess molecular weight on the gel. The gel proteins were transferred to a nitrocellulose membrane using a transfer buffer of 14.4 g/l glycine, 3 g/l of Tris Base, 10% methanol, and 0.05% SDS. The membranes were blocked, probed with the antibody mPA7 (at a concentration of 0.5 ug/ml), and developed using the Invitrogen WesternBreeze® Chromogenic Kit-AntiMouse according to the manufacturer's directions. In the reduced sample of the pancreatic tumor cell membrane samples, a prominent band was observed migrating at about 55 kDa 110%.

Example 5

Isolation of Antigen Ag-PA7

Purified antibody mPA7 was concentrated to approximately 1 mg/ml using a Centricon® YM30concentrator (Millipore Cat. No. 4208). Approximately 1 mg of mPA7 was covalently coupled to 0.35 gram of cyanogen bromide-activated Sepharose® 4B resin (Amersham Pharmacia Biotech Cat. No. 17-0430-01) according to the manufacturer's instructions. Freshly grown HPAF, Colo-205, LnCap, or Panc-1 cells (~2×$10^9$ cells) were harvested from spinner flasks. The cells were pelleted centrifugally, then were resuspended in a total of 15 mL deionized water (dH2O) containing 100 µl of Protease Inhibitor Cocktail (Sigma Cat. No. P8340).

The cell suspension was frozen at −80° C., then thawed. This process was repeated for five cycles in order to disrupt the cells. The cell membranes were collected by centrifugation at 14,000 rpm for 15 minutes at 4° C. in an Eppendorf microcentrifuge.

The cell membrane pellet was resuspended in 2 ml of Hank's Balanced Salt Solution (HBSS, GibcoBRL Cat. No. 14175-079) containing 2% Empigen® BB detergent (Calbiochem Cat. No. 324690) and 50 µl Sigma Protease Inhibitor Cocktail, pH 7.0. The cell membrane preparation was then placed on a rotator overnight at 4° C.

The cell membrane preparation was diluted with HBSS to a final concentration of 1% Empigen® BB. Insoluble cell debris was removed by centrifugation at 14,000 rpm for 15 minutes at 4° C. in an Eppendorf microcentrifuge. The supernatant containing the soluble membrane proteins was collected and stored at −80° C. until used in affinity purification.

The cell membrane extract was thawed, then mixed with the previously prepared mPA7-affinity gel and rotated for 2 hours at 4° C. After incubation, the affinity gel was washed extensively as follows: 5 times with serum- and additive-free HBSS+1.0% Empigen® BB→3 times with serum- and additive-free HBSS+0.5% Empigen® BB→3 times with serum- and additive-free HBSS+0.25% Empigen® BB→2 times with serum- and additive-free HBSS+0.125% Empigen® BB→2 times with serum- and additive-free HBSS alone→1 time with 0.5 M NaCl in $dH_2O$→1 time with PBS.

Each wash consisted of 5.0 mL, with the exception of the 0.5 M NaCl wash, which was 1.5 ml. The antigen was then eluted from the affinity gel with 1.5 ml of 2% acetic acid in dH2O for 2 minutes. The 0.5 M NaCl wash and the acid-eluted antigen were retained, and the sample volumes of each were reduced to ~100 µl using a SpeedVac® (Savant Cat. No. ISS110) on medium heat for ~2.5 hours.

The samples were then precipitated and extracted by the addition of 400 µl methanol and 100 µl chloroform. Samples were vortexed, then 300 µl dH2O was added and mixed gently. The samples were centrifuged at 14,000 rpm for 4 minutes at room temperature in an Eppendorf microcentrifuge. The protein localizes at the interface of the liquid phases, so most of the top layer was discarded. 400 µl methanol was added to the remainder of the samples and mixed gently. The samples were again centrifuged at 14,000 rpm for 4 minutes at room temperature. The supernatant was discarded, and a Speed-Vac® was used to dry the samples completely.

The dried samples were reconstituted by the addition of 28 µl 1×LDS sample buffer (Invitrogen Cat. No. NP007) in preparation for electrophoresis. The samples were heated to 75° C. for 10 minutes, then were centrifuged in a microcentrifuge and vortexed to mix. 25 µl of each sample was loaded into a single lane on a pre-cast NUPAGE® 4-12% gradient gel (Invitrogen Cat. No. NP0322) for subsequent antigen identification. Two microliters were loaded in another lane for Western blotting analysis. Appropriate molecular weight standards were also included on the gel, as were samples of the cell membrane protein extract before and after incubation with the affinity resin. Electrophoresis was performed according to the manufacturer's instructions. The gel was fixed in 50% methanol containing 10% acetic acid for 30 minutes, then was stained using a Colloidal Blue stain (Invitrogen Cat. No. LC6025) according to the manufacturer's instructions. A non-fixed portion of the gel was transferred onto a nitrocellulose sheet (Invitrogen Cat. No. LC2000) for Western blotting, again according to the manufacturer's instructions. The blot was then probed with mPA7 and developed using a Western Blotting Kit (Invitrogen Cat. No. WB7103) to confirm antigen recognition.

Stained protein bands from the NuPAGE® gel were excised using clean scalpel blades and were placed in clean Eppendorf tubes. Excised bands were stored at −20° C. until used for protein identification by mass spectrometry.

Example 6

Characterization of the Antigen to which mPA7 Binds Using MALDI Mass Spectrometry The antigen to which mPA7 binds was isolated as described in Example 5 and subjected to MALDI mass spectroscopy. Eluates of the immunoaffinity column were separated by SDS-PAGE, and the bands were excised and extracted. The gel slice was tryptically digested "in gel" (Gharahdaghi, F., Weinberg, C. R., Meagher, D. A., Imai, B. S., and Mische, S. M. (1999) Electrophoresis 20, 601-605). Extracted peptides were analyzed by matrix-assisted laser desorption/ionization time-of-flight mass spectrometry (MALDI-Tof) on a Kratos, AXIMA CRF. Peptide masses were determined within 100 ppm and a time ion gate with a curved field reflectron was employed for peptide isolation and fragmentation via post-source-decay (PSD). Searches were conducted with the Protein Prospector Programs (Clauser K. R., Baker, P. R., and Burlingame A. L., Analytical Chemistry 71, 2871-(1999) MSFit and MSTag. The antigen was identified as CD46.

Example 7

Characterization of the Epitope on CD46 that mPA7 Binds

To test whether the epitope on CD46 that mPA7 binds is disulfide bond dependent, immunoprecipitation and Western blotting techniques were used. Human colon cancer cell line, HT-29 (ATCC #HTB-38) were lysed by incubating for 5 minutes, on ice, in lysis buffer (HBSS+containing 2% Triton X-100, 2 mM PMSF, 0.1% sodium azide, and 1 tablet per 5 ml lysis buffer of EDTA-free complete mini-protease cocktail (EDTA free complete mini-protease cocktail was obtained from Roche Molecular Biochemicals; all other chemicals were from Sigma Chemicals)). Cells were scraped in lysis buffer and the lysates were collected. Lysates were clarified by centrifugation, 24,000×g for one hour at 4° C. Clarified lysates were first pre-cleared for 2 hours at 4° C. with 5 µl of mouse IgG/BSA conjugated (1 mg/ml) CNBr 4 MB sepharose® beads (Amersham Pharmacia). Mouse IgG/BSA beads were removed, and the pre-cleared lysates were then incubated with 10 µg mPA7 for 2 hours at 4° C. The antigen and mPA7 complex were incubated with 10 µl protein G Sepharose® beads. The beads were then individually washed three times with 1 ml of lysis buffer, followed by three 1 ml washes with HBSS+. Washed beads were eluted by the addition of 30 µl of SDS-PAGE sample buffer in the presence or absence of 20 mM dithiothreitol (DTT) and boiling at 99° C. for 5 minutes. The samples were resolved on a 4-20% Tris-Glycine Novex® gradient gel (Invitrogen), transferred onto 0.2 µm nitrocellulose (Invitrogen) and western blotted with 5 µg/blot of mPA7. For western blotting with mPA7, the nitrocellulose was blocked for 1 hour in blocking buffer. The nitrocellulose was then incubated in a heat sealed plastic pouch containing 1 ml of 5 µg/ml mPA7 diluted in blocking buffer. The nitrocellulose was washed 3 times with PBST before incubation with 10 ml of 1 µg/ml HRP conjugated donkey anti-mouse IgG (heavy and light chain specific, cross adsorbed against bovine, chicken, goat, guinea pig, syrian hamsters, horse, human, rabbit, sheep serum proteins) for 1 hour at room temp. The nitrocellulose was finally washed three times with PBST and visualized by color development using DAB substrate.

Figure 4:
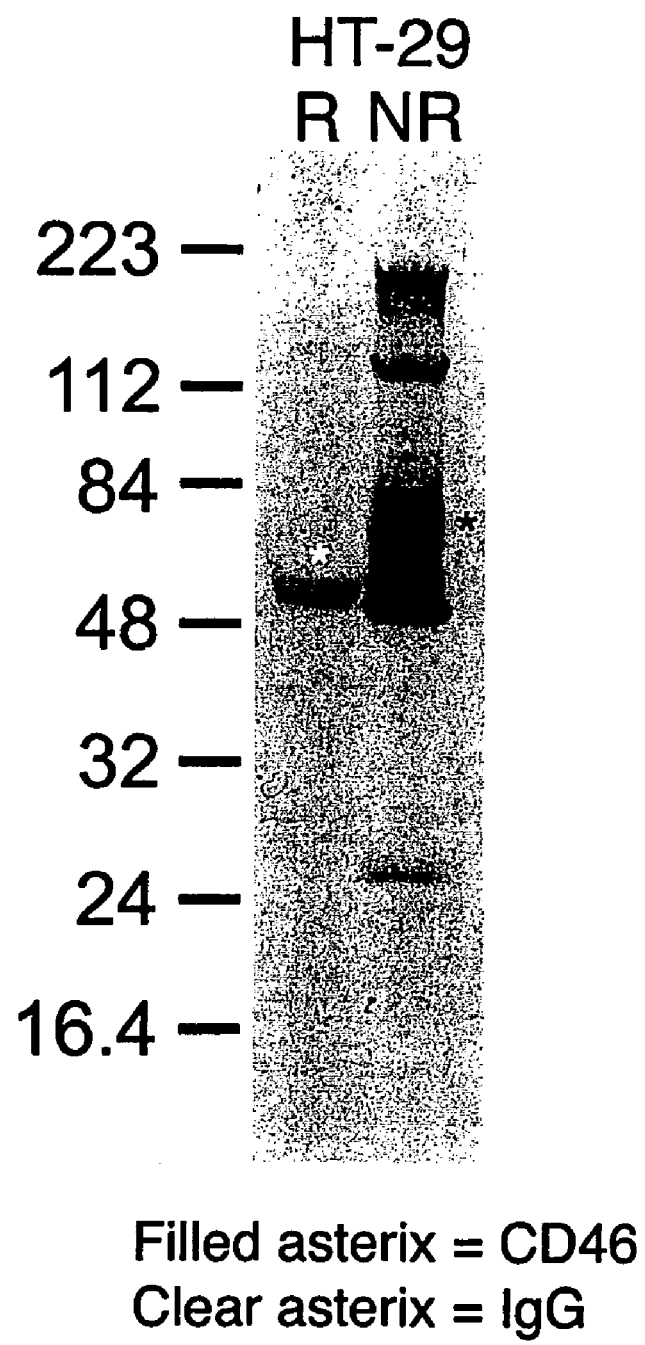
FIG. 4 is a graph which shows the epitope that mPA7 binds is disulfide bond dependent.

As shown in FIG. 4, mPA7 only binds to non-reduced (NR) CD46 (absence of DTT), but does not bind to reduced (R) CD46 (presence of DTT), indicating that the epitope that mPA7 binds is disulfide bond dependent.

Example 8

Immunohistochemistry Methods

Frozen tissue samples from cancer patients were embedded in OCT compound and quick-frozen in isopentane with dry ice. Cryosections were cut with a Leica 3050 CM microtome at thickness of 5 µm and thaw-mounted on vectabound-coated slides. The sections were fixed with ethanol at −20° C. and allowed to air dry overnight at room temperature. The fixed sections were stored at −80° C. until use. For immunohistochemistry, the tissue sections were retrieved and first incubated in blocking buffer (PBS, 5% normal goat serum, 0.1% Tween® 20) for 30 minutes at room temperature, and then incubated with the mPA7 and control monoclonal antibodies diluted in blocking buffer (1 µg/ml) for 120 minutes. The sections were then washed three times with the blocking buffer. The bound monoclonal antibodies were detected with a goat anti-mouse IgG+IgM (H+L) F(ab')$_2$-peroxidase conjugates and the peroxidase substrate diaminobenzidine (1 mg/ml, Sigma cat. No. D 5637) in 0.1 M sodium acetate buffer pH 5.05 and 0.003% hydrogen peroxide (Sigma cat. No. H1009). The stained slides were counterstained with hematoxylin and examined under Nikon microscope. A summary of the results of several experiments using frozen surgical tissue is shown below in Table 1. The percentage of tumors which bind mPA7 is listed and the number binding/total number tested is shown in parentheses.

TABLE 1

Summary of the incidence of the Ag-PA7 antigen occurrence on major tumor types

| Cancer | Ag-PA7 |
|---|---|
| Colon | 75% (3/4) |
| Lung | 100% (8/8) |
| Breast | 80% (8/10) |
| Prostate | 100% (6/6) |
| Renal | 60% (6/10) |
| Pancreas | 100% (1/1) |
| Total | 82% (32/39) |

Example 9

Immunocytochemistry Result from CellArray™

Monoclonal antibody mPA7 was used to test reactivity with various cell lines from different types of tissues. Cells from different established cell lines were removed from the growth surface without using proteases, packed and embedded in OCT compound. The cells were frozen and sectioned, then stained using a standard IHC protocol. The CellAffay™ technology is described in WO 01/43869. Results from the CellArray™ binding experiments are summarized in Table 3. Each cell line is scored as reactive (+) or non-reactive (−).

TABLE 3

Binding of the mPA7 antibody to established human tumor and normal cell lines

| Cell Lines | Organ | Type | Reactivity with mPA7 (respectively) |
|---|---|---|---|
| SK-Ov3 | human ovary | cancerous | + |
| PC3, LnCaP, Du-145 | human prostate | cancerous | −, +, + |
| HT29, SW480, Colo-205 | human colon | cancerous | +, +, + |
| A549, SKMES-1, Rav CA130, CaLu3 | human lung | cancerous | +, +, +, + |
| PANC-1, Capan-1, HF700T, CFPAC-1, HPAF-II, AsPC-1 | human pancreas | cancerous | +, +, +, +, +, + |
| 786-O, Caki-2, A-498 | human renal | cancerous | +, +, + |
| SKBR3, BT474 | human breast | cancerous | +, + |
| hPED | human fetal pancreas | normal | + |
| fh kidney | human fetal kidney | normal | + |
| HMEK, NHEK | human adult endothelial cells | normal | −, − |
| COS-7 | monkey kidney | virus transformed | − |
| AoSMC | human aortic smooth muscle | normal | − |
| WI-38 | human fetal lung fibroblasts | normal | − |
| RL-65 | neonatal rat lung | normal | − |

Example 10

Binding of mPA7 to Normal Tissues

Normal tissue (human) obtained by surgical resection were frozen and mounted as in Example 8. Cryosections were cut with a Leica 3050 CM mictrotome at thickness of 5 µm and thaw-mounted on vectabound-coated slides. The sections were fixed with ethanol at −20° C. and allowed to air dry overnight at room temperature. PolyMICA® Detection kit was used to determine binding of mPA7 to normal tissue. Primary antibody mPA7 was used at a final concentration of 1 ug/ml. The results of staining of normal tissues with mPA7 is shown in Table 4.

TABLE 4

Staining of normal skin structures with mPA7 antibody using frozen tissues and polyMICA visualization

| | |
|---|---|
| Blood vessel wall (smooth muscle) | − |
| Squamous epithelium | + |
| Pilo-erector (smooth muscle) | − |
| Adipocytes | − |
| Hair follicle | + |
| Sebaceous glands | + |

Example 11

Staining Human Lung Carcinoma

FIG. 1 show a photograph of mPA7 staining of a human lung carcinoma. The tumor sample was embedded and frozen section prepared, ethanol fixed and IHC carried out as described for frozen sections. The staining (brown) on the apical surface of luminal epithelium indicated mPA7 binding to the tumor. The adjacent normal tissue which did not bind mPA7 was counterstained with hematoxylin and appeared pale blue, to aid in identifying morphology.

Example 12

Effect of mPA7 on Prostate Cancer Cell Lines

A desired property of an anti-cancer antibody is the ability to inhibit the growth of tumor cells. One methodology for such an evaluation is the decreased growth of cells in vitro upon exposure to an antibody. The ability of the antibodies to reduce cell number in vitro when grown as a monolayer can be assessed using cell monolayers grown in the presence or absence of varying amounts of the purified test or control antibody and the change in the cell number assessed using crystal violet. Crystal violet is a non-specific protein stain and therefore correlates with relative cell number.

Figure 2:
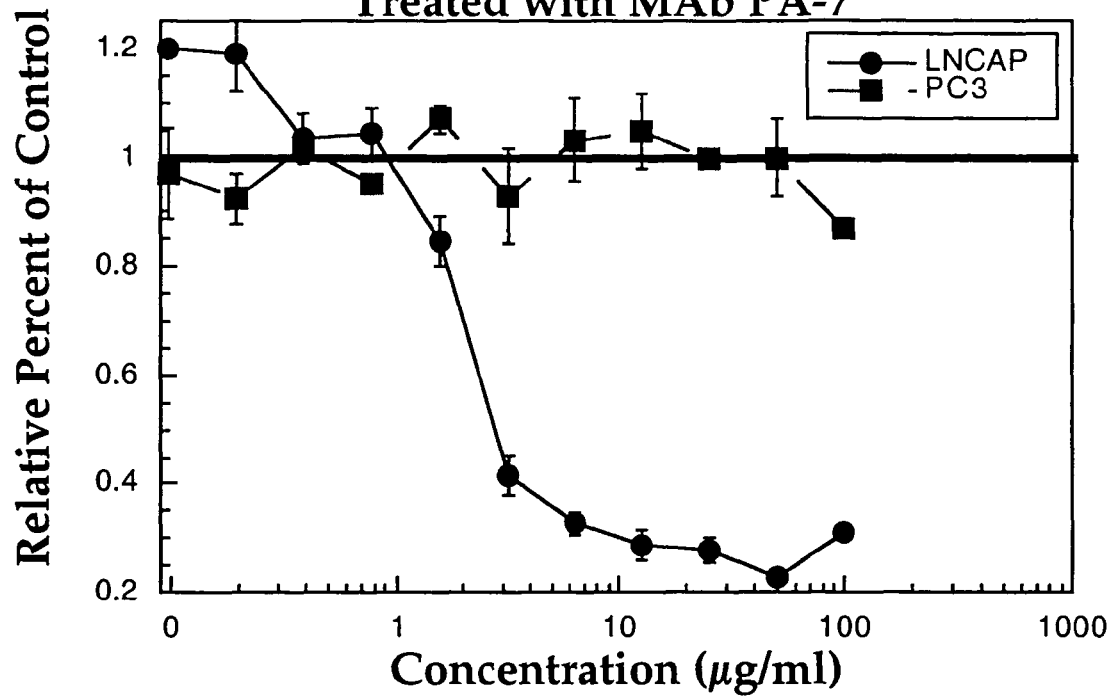
FIG. 2 is a graph that shows inhibition of LnCaP prostatic carcinoma cell growth in a monolayer by mPA7.

Cells of interest were plated and grown in F12/DMEM (1:1) growth medium supplemented with 10% fetal bovine serum in 96 well plates. Two human prostatic carcinoma-derived cell lines were plated at the following densities in duplicate wells of a 96 well dish: LnCap ($1 \times 10^4$ cells/well) and PC3 ($5 \times 10^3$ cells/well). At 24 hours after plating, the indicated antibodies were added to the final concentrations shown on the x axis of FIG. 2. The cells were incubated at 37 degrees Celsius in a humidified incubator at 5% $CO_2$/air for 5 days. At the end of the experiment, the medium was removed and crystal violet solution (0.5% wt/vol in methanol and formaldehyde) was added and the plates incubated for 20 minutes at room temperature. This procedure fixes and stains the cells at the same time. The crystal violet solution was removed by flicking the plate. The plate was then washed three times by flooding with water. After the plate was completely dry, it was read in a plate reader at 540 nm. Alternatively, the dye may be solubilized in 50/50 0.1M sodium citrate (pH 4.2) and ethanol, 200 µl/well. The plate is then sealed with plastic film and shaken until the dye is dissolved. The addition of mPA7 at concentrations between 1.5 µg/ml and 50 µg/ml inhibited LN-CaP cell growth by up to 90%. No effect was seen on the growth of PC3 cells which do not bind mPA7.

Example 13

Effect of mPA7 on Prostate Cancer

Figure 3:
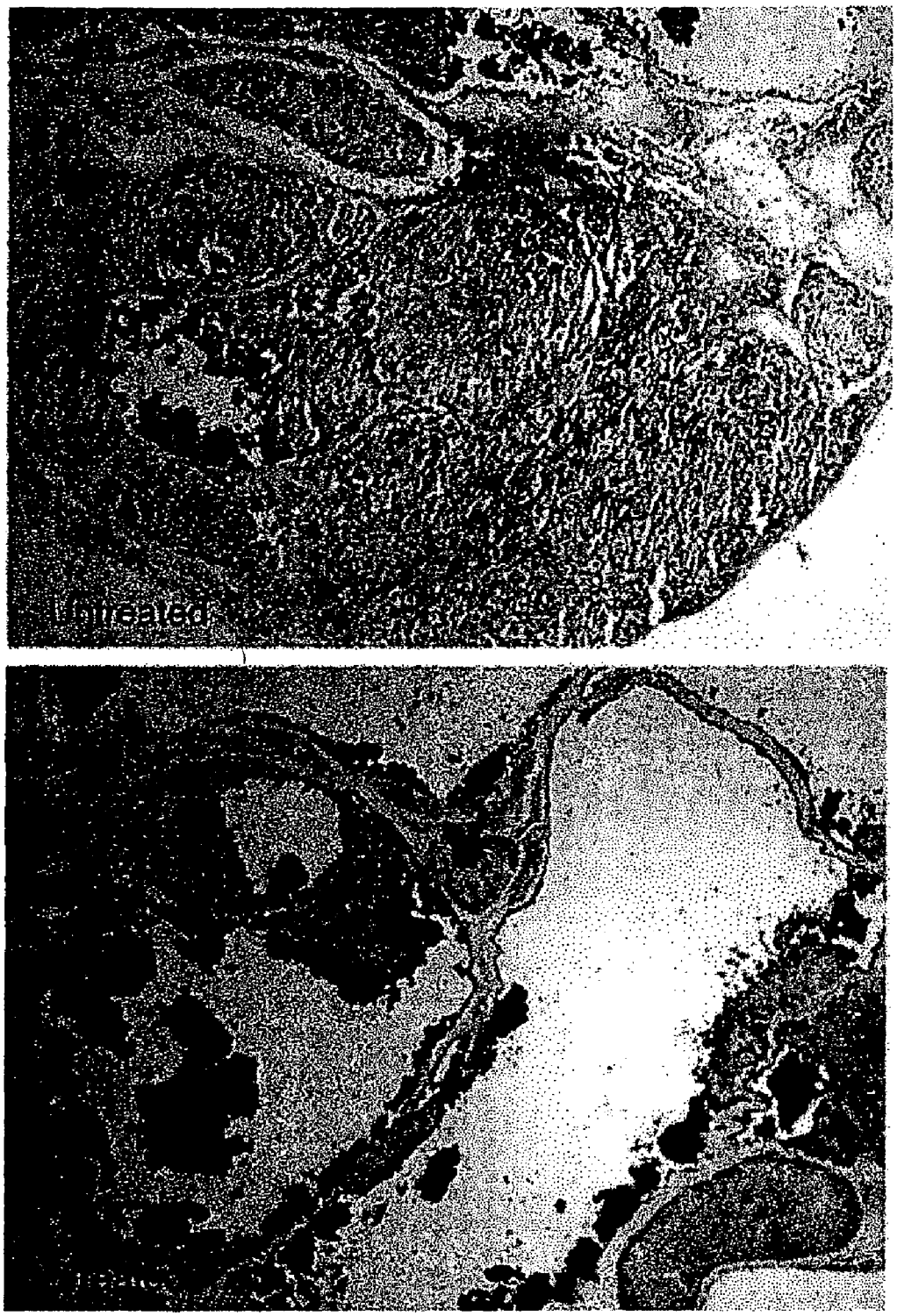
FIG. 3 is a photograph which shows the effect of mPA7 on the LnCaP cell line-derived human prostate tumor xenograft grown in athymic (nu/nu) mice.

A mouse model of human prostate cancer was used to assess the efficacy of mPA7 on human prostate cancer. LN-CaP (human prostate carcinoma cells) and WI38 (human fibroblast cells) were obtained from cell culture. $1 \times 10^5$ cells of each cell type were cast in a collagen gel that was then transplanted under the kidney capsule of a CD1 nude mouse (Charles River, Hollister, Calif.). After ten days of growth, the host kidney of each animal in the treatment and control groups was exposed for observation and recording of tumor growth. Animals were then administered with the first treatment of antibody or the PBS (phosphate buffered saline) excipient. In the treatment group, four doses of mPA7 antibody (100 µg/g body weight of host/dose) in 100 µl of PBS were administered at 3-day intervals intraperitoneally. The control group was injected at the same intervals with 100 µl PBS. Hosts were sacrificed two days after the final dosage was administered. Tumor sizes were recorded and the tumors were fixed in 10% neutral formalin for histology. FIG. 3 shows a photograph of the LN-Cap tumors fixed and embedded in paraffin, then cut in 5 µm sections and stained with hematoxylin and eosin. The upper panel shows untreated prostate cancer tissue from the PBS control group and the bottom panel shows prostate cancer tissue treated with mPA7 following the methods disclosed above. The mPA7 treated LN-Cap tumor shows massive necrosis and hemolysis with the few remaining tumor cells appearing abnormal and apoptotic. The WI-38 cells were unaffected by mPA7 treatment. In subsequent experiments, a similar effect on LN-Cap tumors was seen even when the mPA7 dose was reduced to 50 µg/g body weight for four doses, 50 µg/g body weight for three doses or 5 µg/g body weight for three doses.

In subsequent experiments, tumors derived from the PC3 prostate cancer cell line were grown as described for the LN-Cap cell line. The PC3 tumors, which do not bind mPA7, were unaffected by treatment with three doses of 5 or 50 µg/g body weight of mPA7. These data show that mPA7 is active against in-vivo xenografts of tumors derived from cells which bind the mPA7 antibody, but had no effect on tumors or normal cells which do not bind mPA7.

Example 14

Internalization of mPA7 and Toxin-conjugated Anti-mouse IgG

Mab-ZAP (Advanced Targeting Systems, San Diego, Calif.) is anti-mouse IgG conjugated to saporin, a toxin which inhibits protein synthesis. This toxin is impermeable to the cell membrane. If a monoclonal antibody is bound to a cell-surface antigen which is internalizable, the toxin-conjugate can bind to the bound monoclonal and be internalized, eventually killing the cell. Being dependent upon internalization for demonstration of toxic activity, the Mab-ZAP can serve to evaluate whether or not a given surface antigen will serve as a suitable target for any toxin that is dependent upon internalization to express cell toxic effects. As such, the Mab-ZAP serves as a model for such internalization-dependent toxins such as maytansinoids and calicheamicins.

For testing the internalization of mPA7 and saporin conjugated anti-mouse IgG by tumor cells and effect of killing the tumor cells after internalization of saporin, human prostate tumor cells, LNCaP (ATCC #CRL-1740) were removed from stock flasks with 10 mM EDTA and centrifuged. Cells were resuspended at 50,000/ml in appropriate medium and 100 µl plated per well in 96 well plates. Antibody mPA7 was added immediately to appropriate wells as a 10× concentrate, to make a final concentration of 10 ug/ml. After 15 minutes at room temperature Mab-ZAP (Cat. # IT-04, Advanced Targeting Systems, San Diego Calif.) was added to appropriate wells as 10× concentrate, to make final concentrations from 0.001 pM to $10^4$ pM. After 4 days growth, MTT was added (stock 5 mg/ml PBS, 1:10 dilution in well) for 4 hrs at 37° C. The medium was then removed from all wells and 100 µl/well DMSO was added. The plates was gently swirled to solublize the blue MTT precipitate and the plates were read in a plate reader at 540 nm.

Figure 5:
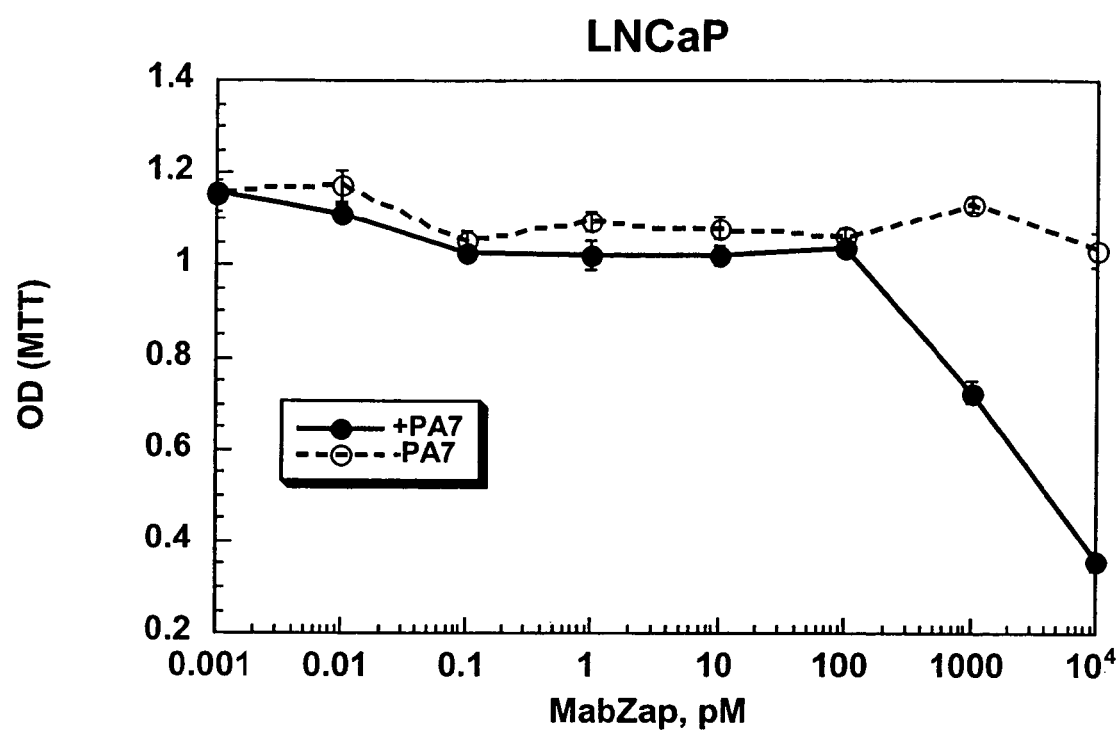
FIG. 5 is a graph shows the effect of mPA7 and Mab-ZAP (an anti-IgG conjugate to saporin) on the growth of human prostate tumor cells LNCaP.

As shown in FIG. 5, there was a decrease in MTT staining in LNCaP in the presence of mPA7 as compared to the staining in the absence of mPA7 when Mab-ZAP was added above 100 pM, indicating the growth of human prostate tumor cells LNCaP was inhibited in the presence of mPA7 and Mab-ZAP, and mPA7 and toxin-conjugated anti-mouse IgG were internalized in LNCaP. When Mab-ZAP was used at $10^4$ pM, there was more than 50% of decrease in MTT staining, corresponding to more than 50% inhibition of the growth of LNCaP by binding of mPA7 and Mab-ZAP.

Similar tests were performed in human prostate cancer cells, 22RV1 (ATCC CRL-2505); human ovarian cancer cells, SK-OV-3 (ATCC #HTB 77); human breast cancer cells, SK-BR-3 (ATCC #HTB30); human colon cancer cells, COLO 205 (ATCC #CCL 222). In all of the above cancer cells tested, mPA7 and Mab-ZAP were internalized and inhibited growth of these cells.

Similar tests were also performed in normal human umbilical venous endothelial cells (HUVEC) (BioWhittaker/Clonetics catalogue #C2519A). When HUVEC cells were cultured in non-confluent condition, i.e., cells were allowed to divide and grow, mPA7 and Mab-ZAP were internalized and inhibited growth of these cells. However, when HUVEC cells were cultured in confluent condition, i.e., cells were generally not dividing, mPA7 and Mab-ZAP were not internalized or not toxic to these cells under the conditions used. This result suggests that binding of mPA7 linked to a therapeutic agent to non-dividing HUVEC (which is similar to normal condition in human) is not toxic to these cells. This result also suggests that mPA7 linked to a therapeutic agent may be used as an anti-angiogenesis agent.

It is understood that the examples and embodiments described herein are for illustrative purposes only and that various modifications or changes in light thereof will be suggested to persons skilled in the art and are to be included within the spirit and purview of this application. All publications, patents and patent applications cited herein are hereby incorporated by reference in their entirety for all purposes to the same extent as if each individual publication, patent or patent application were specifically and individually indicated to be so incorporated by reference.

I claim:

1. A method of inhibiting growth of cancerous cells in a human individual comprising administering to the individual an effective amount of a composition comprising: (i) a chimeric or humanized antibody and (ii) a pharmaceutically acceptable excipient, wherein:

(A) said chimeric or humanized antibody comprises the three complementarity determining regions (CDRs) from the heavy chain and the three complementarity determining regions (CDRs) from the light chain of antibody mPA7 produced by a host cell with a deposit number of ATCC No. PTA-3706, and further comprises constant regions sufficient to induce an active immune response against cancerous cells (B) said chimeric or humanized antibody specifically binds to the human CD46 antigen at the epitope recognized by antibody mPA7;

wherein said cancerous cells express said human CD46 antigen having the epitope recognized by antibody mPA7 on their cell surface, and bind said chimeric or humanized antibody, which induces an active immune response against said cancerous cells and inhibits their growth.

2. The method of claim 1, wherein the antibody is linked to a therapeutic agent.

3. The method of claim 1, wherein the cancerous cells are prostate.

4. The method of claim 1, wherein the antibody is a humanized antibody that comprises said three CDRs from the heavy chain and said three CDRs of the light chain of antibody mPA7 grafted into a human supporting framework region.

5. The method of claim 1, wherein the antibody is a chimeric antibody that comprises heavy chain and light chain constant regions from constant regions of a human antibody.

6. The method of claim 2, wherein the therapeutic agent is a toxin, a radioactive compound, or a chemotherapeutic agent.

* * * * *